United States Patent
Au et al.

(10) Patent No.: US 9,743,990 B2
(45) Date of Patent: *Aug. 29, 2017

(54) TENSION CONTROL IN ACTUATION OF MULTI-JOINT MEDICAL INSTRUMENT

(71) Applicant: Intuitive Surgical Operations, Inc., Sunnyvale, CA (US)

(72) Inventors: Samuel Kwok Wai Au, Mountain View, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 14/751,636

(22) Filed: Jun. 26, 2015

(65) Prior Publication Data

US 2015/0289942 A1  Oct. 15, 2015

Related U.S. Application Data

(63) Continuation of application No. 12/945,734, filed on Nov. 12, 2010, now Pat. No. 9,101,379.

(51) Int. Cl.
*A61B 34/00* (2016.01)
*A61B 19/00* (2006.01)
*A61B 34/30* (2016.01)

(52) U.S. Cl.
CPC .......... *A61B 19/2203* (2013.01); *A61B 34/30* (2016.02); *A61B 2034/301* (2016.02); *A61B 2034/306* (2016.02); *A61B 2034/715* (2016.02)

(58) Field of Classification Search
CPC .... A61B 2019/2211; A61B 2019/2238; A61B 2019/2246; A61B 19/2203;

(Continued)

(56) References Cited

U.S. PATENT DOCUMENTS 6,424,885 B1   7/2002  Niemeyer et al.
6,493,608 B1   12/2002  Niemeyer
(Continued)

FOREIGN PATENT DOCUMENTS

JP    H06332535 A    12/1994
WO   WO-2007111737 A2   10/2007
WO   WO-2011143069 A1   11/2011

OTHER PUBLICATIONS

Kumar, Rajesh et al., "Experiments with a Steady Hand Robot in Constrained Compliant Motion and Path Following", 1999, pp. 92-97, IEEE.

(Continued)

*Primary Examiner* — Katrina Stransky
(74) *Attorney, Agent, or Firm* — Fish & Richardson P.C.

(57) ABSTRACT

A medical instrument system includes a plurality of joints, a plurality of actuators, and a plurality of transmission systems. The transmission systems have proximal ends respectively coupled to the actuators. Each of the transmission systems have a distal end attached to an associated one of the joints to allow the transmission of a force for articulation of the medical instrument system. The system also includes a sensor coupled to measure a configuration of the medical instrument; and a control system coupled to receive configuration data, including a current configuration of a tip of the medical instrument from the sensor and a desired configuration of the tip of the medical instrument. Using the difference between the desired configuration and the current configuration of the tip of the medical instrument, the control system generates control signals for the actuators that cause the actuators to apply a set of tensions to the plurality of transmission systems.

20 Claims, 8 Drawing Sheets

(58) Field of Classification Search
CPC .... A61B 2019/2242; A61B 2019/2234; A61B 34/30; A61B 2034/306; A61B 2034/301
See application file for complete search history.

(56) References Cited

U.S. PATENT DOCUMENTS

| | | |
|---|---|---|
| 6,817,974 B2 | 11/2004 | Cooper et al. |
| 7,320,700 B2 | 1/2008 | Cooper et al. |
| 7,689,320 B2 | 3/2010 | Prisco et al. |
| 7,720,322 B2 | 5/2010 | Prisco |
| 7,741,802 B2 | 6/2010 | Prisco et al. |
| 7,819,859 B2 | 10/2010 | Prisco et al. |
| 7,843,158 B2 | 11/2010 | Prisco et al. |
| 9,101,379 B2 | 8/2015 | Au et al. |
| 2007/0156019 A1 | 7/2007 | Larkin et al. |
| 2007/0287992 A1 | 12/2007 | Diolaiti et al. |
| 2008/0065105 A1 | 3/2008 | Larkin et al. |
| 2009/0012533 A1 | 1/2009 | Barbagli et al. |
| 2009/0088774 A1 | 4/2009 | Swarup et al. |
| 2009/0123111 A1 | 5/2009 | Udd |
| 2010/0082041 A1 | 4/2010 | Prisco |
| 2010/0331820 A1 | 12/2010 | Prisco et al. |
| 2010/0332033 A1 | 12/2010 | Diolaiti et al. |
| 2011/0009880 A1 | 1/2011 | Prisco et al. |
| 2012/0123441 A1 | 5/2012 | Au et al. |

OTHER PUBLICATIONS

PCT/US2011/058376 International Search Report and Written Opinion of the International Searching Authority, mailed Feb. 3, 2012, 8 pages.

Stefanini, Cesare et al., "Modeling and Experiments on a Legged Microrobot Locomoting in a Tubular, Compliant and Slippery Environment," The International Journal of Robotics Research, 2006, pp. 551-560, vol. 25, SAGE Publications.

Szakaly, Zoltan et al., "Force-Reflective Teleoperated system with shared and complaint control capabilities," Proc. NASA Conf. Space Telerobotics, 1989, 14 Pages Total.

Vertut. Jean and Phillipe Coiffet, Robot Technology; Teleoperation and Robotics Evolution and Development, English translation, Prentice-Hail, Inc., Inglewood Cliffs, NJ, USA 1986, vol. 3A, 332 pages.

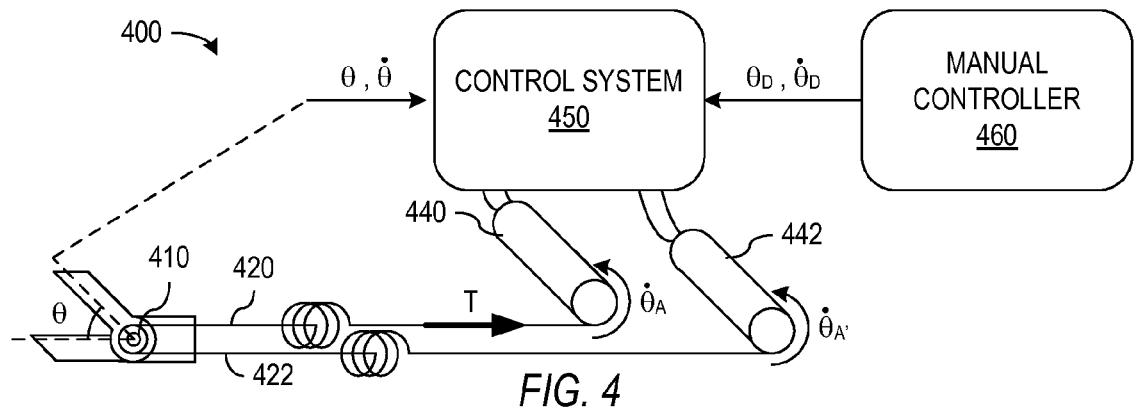
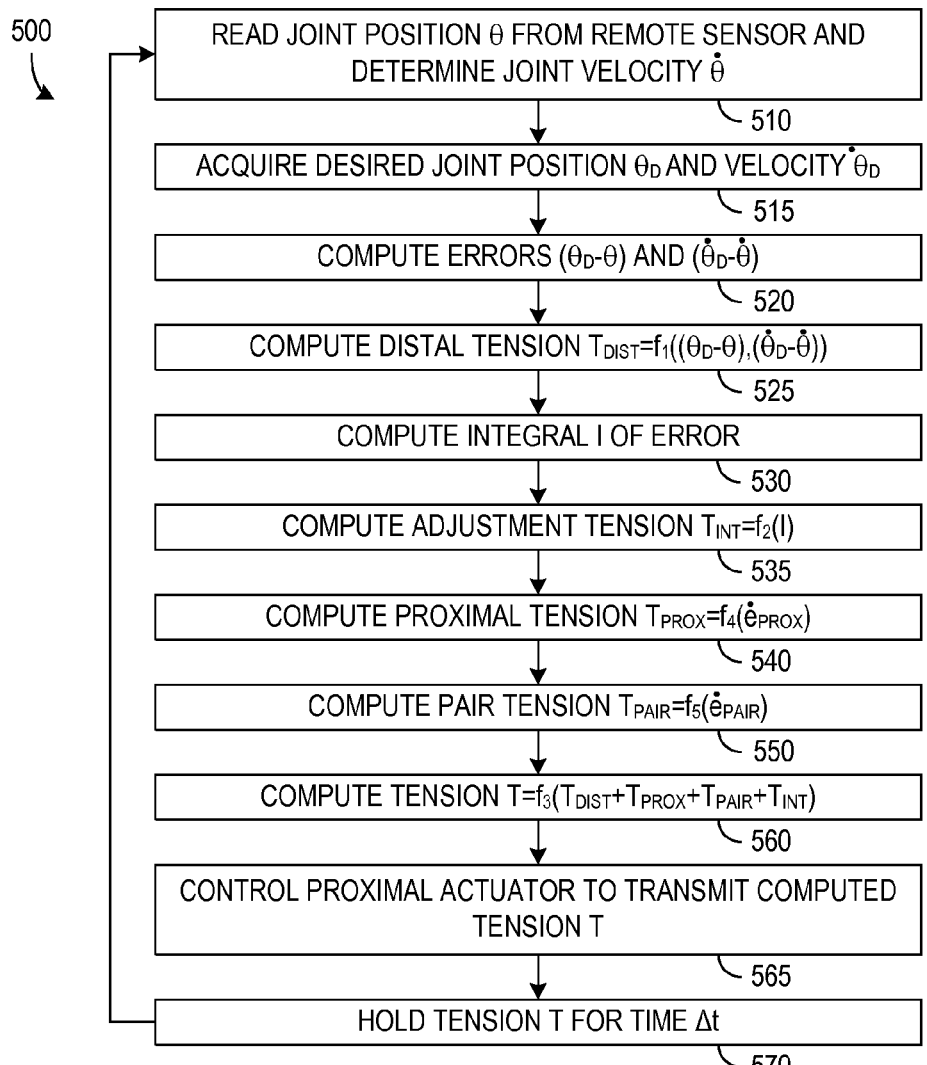
FIG. 5A

TENSION CONTROL IN ACTUATION OF MULTI-JOINT MEDICAL INSTRUMENT

This application is a continuation of U.S. patent application Ser. No. 12/945,734, filed on Nov. 12, 2010, which is incorporated by reference herein in its entirety.

BACKGROUND

Minimally invasive medical procedures often employ instruments that are controlled with the aid of a computer or through a computer interface. FIG. 1, for example, shows a robotically controlled instrument 100 having a structure that is simplified to illustrate basic working principles of some current robotically controlled medical instruments. (As used herein, the terms "robot" or "robotically" and the like include teleoperation or telerobotic aspects.) Instrument 100 includes a tool or end effector 110 at the distal end of an elongated shaft or main tube 120. In the illustrated example, end effector 110 is a jawed tool such as forceps or scissors having separate jaws 112 and 114, and at least jaw 112 is movable to open or close relative to jaw 114. In use during a medical procedure, end effector 110 on the distal end of main tube 120 may be inserted through a small incision in a patient and positioned at a work site within the patient. Jaws 112 may then be opened and closed, for example, during performance of surgical tasks, and accordingly must be precisely controlled to perform only the desired movements. A practical medical instrument will, in general, require many degrees of freedom of movement in addition to opening and closing of jaws 112 and 114 in order to perform a medical procedure.

The proximal end of main tube 120 attaches to a transmission or drive mechanism 130 that is sometimes referred to as backend mechanism 130. Tendons 122 and 124, which may be stranded cables, rods, tubes, or combinations of such structures, run from backend mechanism 130 through main tube 120 and attach to end effector 110. A typical surgical instrument would also include additional tendons (not shown) that connect backend mechanism 130 to other actuated members of end effector 110, a wrist mechanism (not shown), or actuated vertebrae in main tube 120, so that backend mechanism 130 can manipulate the tendons to operate end effector 110 and/or other actuated elements of instrument 100. FIG. 1 illustrates jaw 112 as having a pin joint structure 116 that provides a single degree of freedom for movement of jaw 112. Two tendons 122 and 124 are attached to jaw 112 and to a pulley 132 in backend mechanism 130, so that rotations of pulley 132 cause jaw 112 to rotate.

Pulley 132 is attached to a drive motor 140, which may be at the end of a mechanical arm (not shown), and a control system 150 electrically controls drive motor 140. Control system 150 generally includes a computing system along with suitable software, firmware, and peripheral hardware. Among other functions, control system 150 generally provides a surgeon or other system operator with an image (e.g., a stereoscopic view) of the work site and end effector 110 and provides a control device or manipulator that the surgeon can operate to control the movement of end effector 110. The software or firmware needed for interpretation of user manipulations of the control device and for generation of the motor signals that cause the corresponding movement of jaw 112 are generally complex in a real robotic medical instrument. To consider one part of the control task, the generation of the control signals for drive motor 140 commonly employs the relationship between the angle or position of jaw 112 and the angle or position of drive motor 140 or pulley 132 in backend mechanism 130. If the tendons 122 and 124 are rigid (e.g., if stretching of tendons is negligible), control system 150 can use a direct relationship between the angular position of drive motor 140 and the angular position of jaw 112 as defined by the geometry of instrument 100 in determining the control signals needed to move jaw 112 as a surgeon directs. Minor stretching of tendons 122 and 124, for example, under a working load, can be handled by some mathematical models relating motor position to effector position. However, if the mechanical structure including end effector 110, tendons 122 and 124, and backend mechanism 130 has a high degree of compliance, a relationship between the angular position of motor 140 (or pulley 132) and the angular position of jaw 112 may be difficult or impossible to model with sufficient accuracy for a medical instrument. Accordingly, such systems require control processes that do not rely on a fixed relationship between the applied actuator control signals and the position of the actuated elements.

It should be noted that in the following, the joint of the medical instrument can be a pin joint structure or a structure that provides one or more degrees of freedom of motion to the instrument tip. For instance a joint can be a continuously flexible section or a combination of pin joints that approximates a continuously flexible section or a single rotary joint that is not purely revolute but provides also some rolling joint. See, for example, U.S. Pat. No. 7,320,700, by Cooper et Al., entitled "Flexible Wrist for Surgical Tool," and U.S. Pat. No. 6,817,974, by Cooper et Al., entitled "Surgical Tool Having a Positively Positionable Tendon-Actuated Multi-disk Wrist Joint."

It should also be noted that in the state of the art of control of medical robotic instruments, the actuator positions are servo controlled to produce the desired instrument tip motion or position. Such an approach is effective as long as the transmission systems between the actuators and the instrument joints are rigid for all practical purposes. See, for example, U.S. Pat. No. 6,424,885, entitled "Camera Referenced Control in a Minimally Invasive Surgical Apparatus." Such an approach can also be effective if the flexibility of the transmission system can be modeled exactly and a model included in the controller as described in U.S. Pat. App. Pub. No. 2009/0012533 A1, entitled "Robotic Instrument Control System" by Barbagli et Al.

SUMMARY

In accordance with an aspect of the invention, control systems and methods for an instrument having multiple degrees of freedom use differences between a current configuration/velocity of the instrument and a desired configuration/velocity of the instrument to determine and control the forces that proximal actuators apply to the instrument through a set of transmission systems. The use of applied force and feedback indicating the resulting configuration of a medical instrument allows robotic control of the medical instrument, even if transmission systems of the instrument have non-negligible compliance between the proximal actuators and remote actuated elements. The feedback approach particularly allows precise instrument operation even when the configuration of the instrument cannot be directly inferred from the positions of the proximal actuators.

In one embodiment of the invention, the configuration of an end effector or tip is measured or otherwise determined, and the differences between the current and desired configurations of the tip are employed in determining the required joint torques and the applied forces needed to achieve the desired tip configuration. Embodiments of this control method can allow selection of the dynamic behavior of the tip, for example, to facilitate the instrument interaction with tissue, while permitting flexibility in other portions of the instrument.

In another embodiment of the invention, the configuration of each joint in an instrument is measured, and the differences between current and desired joint configurations are used to determine the actuator forces needed to move all of the joints to desired configurations.

One specific embodiment of the invention is a medical system that includes multiple joints, actuators, and transmission systems. The transmission systems have proximal ends respectively coupled to the actuators, and each of the transmission systems has a distal end attached to an associated one of the joints to allow the transmission of a force for articulation of the associated joint. A sensor in the medical system measures configuration of the joints or the instrument tip, and a control system that operates the actuators to apply forces to the transmission systems, receives the configuration measurements from the sensor and uses the configuration measurements to determine the actuation forces applied to the transmission systems.

Another specific embodiment of the invention is a method for controlling a medical instrument. The method includes: measuring a configuration for a plurality of joints of the medical instrument; receiving a command indicating a desired configuration of the medical instrument; determining tensions respectively in transmission systems that connect respective actuators to the joints, and operating the actuator to apply the forces respectively to the transmission systems. The determination of the applied forces is independent of positions of the actuators.

BRIEF DESCRIPTION OF THE DRAWINGS

FIG. 4 schematically illustrates a robotic medical system and particularly shows quantities used in an embodiment of the invention that controls a remote joint connected to actuators through compliant transmission systems.

FIG. 5A is a flow diagram of a control process in accordance with an embodiment of the invention.

Use of the same reference symbols in different figures indicates similar or identical items.

DETAILED DESCRIPTION

In accordance with an aspect of the invention, a medical instrument can be controlled via transmission systems that do not provide fixed relationships between actuator positions and joint positions. In particular, the actions of a system operator (e.g., a surgeon) can indicate a currently desired configuration/velocity for the medical instrument, while a sensor measures the actual configuration/velocity of the instrument. Forces, tensions, or torques can then be selected according to the desired and measured configurations and applied through the transmission systems to move the instrument toward its desired configuration. The selection criteria for the applied force, tension, or torque can be altered if prior selections of the applied force, tension, or torque resulted in the joint overshooting or failing to reach a desired position.

Figure 2:
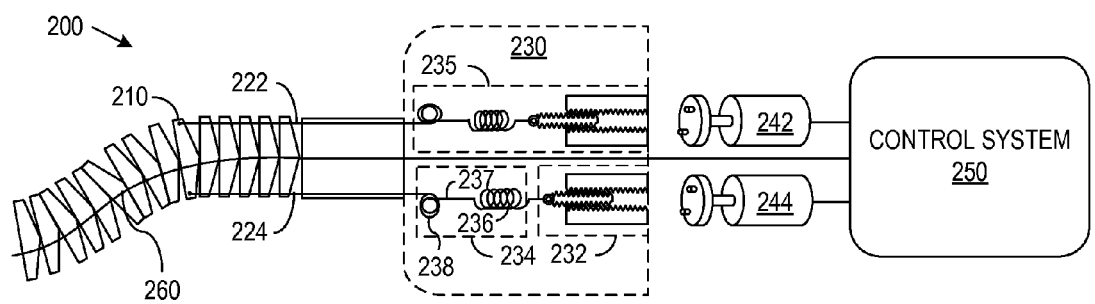
FIG. 2 illustrates a medical instrument that can be operated using a control process in accordance with an embodiment of the invention that controls the force applied through a compliant transmission system to control an articulated vertebra of the instrument.

FIG. 2 illustrates a portion of a compliant medical instrument 200 having a transmission system such as described by U.S. patent application Ser. No. 12/494,797, entitled "Compliant Surgical Device," which is hereby incorporated by reference in its entirety. Instrument 200 includes a jointed element 210 that is manipulated through control of the respective tensions in tendons 222 and 224. In general, instrument 200 may contain many mechanical joints similar to jointed element 210, and each joint may be controlled using tendons similar to tendons 222 and 224. In an exemplary embodiment, instrument 200 is an entry guide that can be manipulated to follow a natural lumen within a patient. An entry guide would typically include a flexible outer sheath (not shown) that surrounds vertebrae (including element 210) and provide one or more central lumens through which other medical instruments can be inserted for access to a work site. Compliance is particularly desirable in entry guides to prevent an action or reaction of the entry guide from harming surrounding tissue that may move or press against the entry guide. However, other types of medical instruments may also benefit from compliant drive mechanisms of the type illustrated in FIG. 2.

Instrument 200 includes a backend mechanism 230 that with tendons 222 and 224 provides a compliant transmission system connecting to jointed element 210 to drive motors 242 and 244. In particular, backend mechanism 230 includes spring systems 235 attached to tendons 222 and 224 and drive motors 242 and 244. Each spring system 235 in FIG. 2 includes a mechanical drive system 232 and a constant force spring 234. Each drive system 232 couples a motor 242 or 244 and converts rotational motion of the drive motor 242 or 244 into linear motion that changes the constant force applied by the associated constant force spring 234 to tendon 222 or 224. In the illustrated embodiment, each constant force spring 234 includes a conventional Hooke's law spring 236 and a cam 238. Each spring 236 connects to an associated drive system 232 so that the linear motion of drive system 232 moves a proximal end of the spring 236. Each cam 238 has a first guide surface on which a cable 237 attached to the distal end of the associated spring 236 attaches and rides and a second guide surface on which a portion of tendon 222 or 224 attaches and rides. The guide surfaces of each cam 238 generally provide different moment arms for the action of the attached cable 237 and the attached tendon 222 or 224 and are shaped so that the tension in tendon 222 or 224 remains constant as the paying out or hauling in of a length of tendon 220 or 224 changes the force applied by the attached spring 236. Each surface of each cam 238 may be a spiral surface that extends for one or more revolutions in order to provide the desired range of movement of the tendon 222 and 224 while maintaining a constant tension in tendon 222 or 224.

Each drive system 232 controls the position of the proximal end of the corresponding spring 236 and thereby influences the amount of baseline stretch in the corresponding spring 236 and the tension in the attached tendon 222 or 224. In operation, if a drive system 232 in a spring system 235 pulls on the attached spring 236, the spring 236 begins to stretch, and if the element 210 and tendon 222 or 224 attached to the spring system 235 are held fixed, the force that spring 236 applies to cam 238 increases and therefore the tension in the attached cable 222 or 224 increases. Accordingly, the tensions in tendons 222 and 224 depend linearly (in accordance with Hooke's law, the moment arms of cam 238, and the spring constant of spring 236) on movement of the proximal ends of respective springs 236, but each spring system 235 behaves asymmetrically, i.e., acts with constant force in response to external or distal forces that move tendon 222 or 224. Constant force spring 234 and drive system 232 can be alternatively implemented in a variety of ways such as those described further in above-referenced U.S. patent application Ser. No. 12/494, 797.

Jointed element 210 has a single degree of freedom of motion (e.g., rotation about an axis) and generally moves when drive motor 242 or 244 rotates a drive system 232 to change the force applied by the attached constant force spring 238. However, this drive mechanism is compliant so that external forces can move element 210 without a corresponding rotation of drive system 232. As a result, there is no fixed relationship between the position or orientation of jointed element 210 and the position of drive system 232 or drive motor 242. In accordance with an aspect of the invention, control system 250 uses a sensor 260 to measure the orientation of element 210. Sensor 260 may be, for example, a shape sensor, which can sense the shape of jointed element 210 along a length of instrument 200 including element 210. Some examples of shape sensors are described in U.S. Pat. App. Pub. No. US 2007/0156019 A1 (filed Jul. 20, 2006), entitled "Robotic Surgery System Including Position Sensors Using Fiber Bragg Gratings" by Larkin et al., and U.S. patent application Ser. No. 12/164, 829 (filed Jun. 30, 2008) entitled "Fiber optic shape sensor" by Giuseppe M. Prisco, both of which are incorporated herein by reference. However, any sensor capable of measuring an angular position of jointed element 210 could alternatively be used. A control process as described further below uses such measurements for calculation of applied forces needed to manipulate jointed element 210.

Instrument 200 has "backdriving" capability when backend mechanism 230 is detached from a motor pack, constant force springs 235 still keep tendons 222 and 224 from slacking and allow the distal portion of instrument to be manually arranged (or posed) without damaging backend mechanism 230 or creating slack in tendon 222 or 224. This "backdriving" capability is generally a desirable property of a surgical instrument, particularly an instrument with a flexible main tube that may be bent or manipulated during instrument insertion while the instrument is not under active control by control system 250. For example, instrument 200 can be manually posed, and the tendons within the main shaft do not experience undue tension or slack.

Figure 3A:
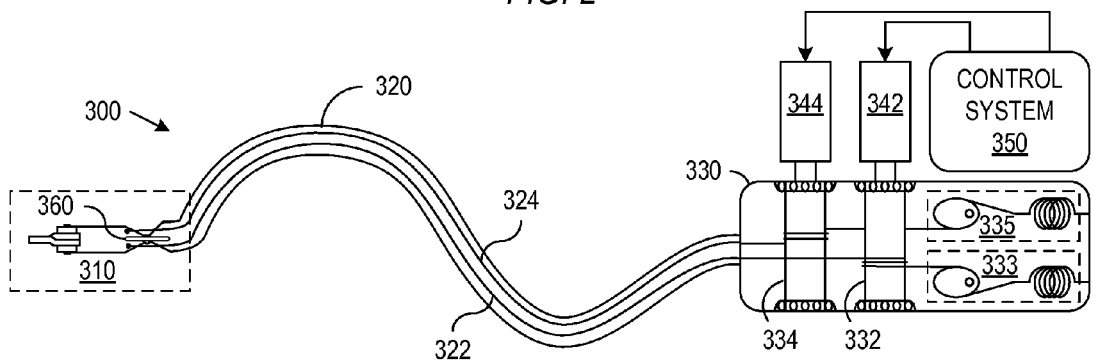
FIG. 3A illustrates a medical instrument in which a control process in accordance with an embodiment of the invention can operate with a transmission system having minimum and maximum force transfer to operate a mechanical joint.

Another example of a compliant transmission system for a joint in a medical instrument is illustrated in FIG. 3A. FIG. 3A shows an exemplary embodiment of a medical instrument 300 that uses an actuation process that permits a drive motor to freewheel or a drive tendon to slip relative to the drive motor during instrument operation as described in U.S. patent application Ser. No. 12/286,644, entitled "Passive Preload and Capstan Drive for Surgical Instruments," which is hereby incorporated by reference in its entirety. Medical instrument 300 has an end effector 310 at the end of a main tube 320, and a backend mechanism 330 manipulates tendons 322 and 324, which run through main tube 320, to control a degree of freedom of motion of end effector 310. In the illustrated embodiment, tendons 322 and 324 attach to a mechanical member in end effector 310 such that tensions in tendons 322 and 324 tend to cause end effector 310 to rotate in opposite directions about a pivot joint structure.

Figure 3B:
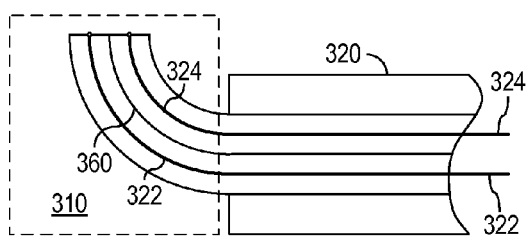
FIG. 3B shows an embodiment of the invention in which a joint includes continuously flexible structure.
Figure 3C:
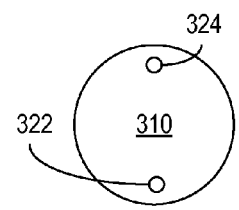
FIG. 3C illustrates positions of a pair of tendons used to control a single degree of freedom of motion in the joint of FIG. 3B.

The joint structure of FIG. 3A is only an example, and other joint mechanisms that provide a single degree of freedom of motion in response to tensions applied to a pair of tendons could be employed in alternative embodiments of the invention. FIG. 3B, for example, illustrates an embodiment in which joint 310 such as commonly found in catheters, endoscopes for the gastrointestinal tract, the colon, and the bronchia; guide wires; or other endoscopic instruments such as graspers and needles used for tissue sampling. that is able to flex or bend in response to forces applied through tendons 322 and 324. The catheter joint may simply include an extrusion of a plastic material that bends in response to a differential in the tension in tendons 322 and 324. In one configuration, tendons 322 and 324 extend through lumens within the catheter and attach to the end of the catheter as shown in FIG. 3C. Accordingly, the forces in tendons 322 and 324 can be used to bend the catheter in the direction corresponding to the tendon 322 or 324 having greater tension. Bending of the catheter may be used, for example, to steer the catheter during insertion. In the embodiment of FIG. 3B, distal sensor 360 can measure the bend angle of the distal portion of the catheter to measure or compute the "joint" angle and velocity. In one particular embodiment, the bend angle can be defined as a tip orientation of the catheter with respect to the base of the distal flexible portion of the catheter. The backend and control architecture for catheter joint 310 of FIG. 3B can be identical to that of the embodiment of FIG. 3A, except that the measured joint angle and velocity can be converted to tendon position and velocity by multiplication of the distance between the actuator cable lumen and the center of the distal flexible portion.

Backend mechanism 330, which attaches to the proximal end of main tube 320, acts as a transmission that converts torques applied by drive motors 342 and 344 into tensions in respective tendons 322 and 324 and forces or torques applied to an actuated joint in end effector 310. In the illustrated embodiment, drive motors 342 and 344 can be direct drive electrical motors that directly couple to capstan 332 and 334 around which respective tendons 322 and 324 wrap. In particular, tendon 322 wraps for a set wrapping angle (that could be less than a full turn or as large as one or more turns) around the corresponding capstan 332 and has an end that is not affixed to capstan 332 but extends from the capstan 332 to a passive preload system 333. Similarly, tendon 324 wraps for a set wrapping angle around the corresponding capstan 334 and has an end extending from the capstan 334 to a passive preload system 335. Since tendons 322 and 324 are not required to be permanently attached to capstans 332 and 334, tendon 322 and 324 may be able to slip relative to capstans 332 and 334 and relative to the shaft of drive motors 342 and 344 that respectively couple to capstans 332 and 334.

The proximal end of tendons 322 and 324 attach to respective passive preload systems 333 and 335, each of which is implemented in FIG. 3A as a cam and a Hooke's law spring that together act as a constant force spring. Passive preload systems 333 and 335 are biased, so that systems 332 and 334 apply non-zero forces or tensions to tendons 322 and 324 throughout the range of motion of instrument 300. With this configuration, when capstans 332 and 334 are free to rotate, passive preload systems 333 and 335 control the tensions in tendons 322 and 324 and avoid slack in tendons 322 and 324 by pulling in or letting out the required lengths of tendons 322 and 324. When backend mechanism 330 is detached from motors 342 and 344, passive preload systems 333 and 335 still keep tendons 322 and 324 from slacking and allow end effector 310 and main tube 320 (when flexible) to be manually arranged (or posed) without damaging backend mechanism 330 or creating slack in tendon 322 or 324. Accordingly, instrument 300 also has "backdriving" capability similar to that described above for instrument 200 of FIG. 2.

End effector 310 can be operated using drive motors 342 and 344 under the active control of control system 350 and human input (e.g., master control input in a master-slave servo control system). For example, when motor 342 pulls on tendon 322, the motor torque is transferred as an applied tension in the distal portion of tendon 322. (A maximum tension that capstan 332 can apply to proximal portion of tendon 322 depends on a tension at which tendon 322 begins to slip relative to captain 332, but in general, the maximum tension actually used can be selected to prevent tendons 322 and 324 from slipping on capstans 332 and 334.) At the same time, when turning off the power to motor 344, allowing motor 344 and capstan 334 to freewheel, tendon 324 can be kept at its minimum tension that is the constant force that passive preload system 335 applies to proximal end of tendon 324 through the capstan 334. The larger tension in tendon 322 then tends to cause end effector 310 to rotate counterclockwise in FIG. 3A. Similarly, turning off power to motor 342 and powering motor 344 to apply force through tendon 324 to end effector 310 tends to cause end effector 310 to rotate clockwise in FIG. 3A. The ability of motor 342 and 344 to freewheel while tendons 322 and 324 are under tension and the acceptance of slippage of tendons 322 and 324 on capstans 332 and 334 do not permit control system 350 to rely on a fixed relationship between the angular positions of motor 340 and end effector 310. However, control system 350 can use a sensor 360 to measure the angular position of end effector 310 relative to the joint actuated through tendons 322 and 324.

Figure 1:
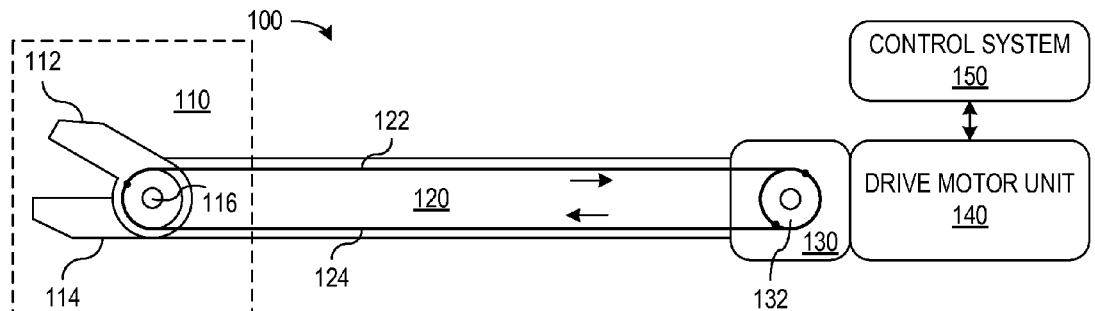
FIG. 1 illustrates features of a known robotically controlled medical instrument.

The instruments of FIGS. 2, 3A, and 3B may have transmission systems between actuators and actuated joints provide compliance that is desirable, particularly for instruments with a flexible main tube. However, transmission systems with compliance may also occur in more traditional instruments. For example, the known instrument of FIG. 1 may use sheathed or Bowden cables in sections of the instrument that bend and rod elements in straight sections. The rod elements can reduce stretching that interferes with the direct relationship of actuator and joint positions. However, it may be desirable in some applications to use tendons of more flexible material (e.g., polymer tendons where electrical insulation or minimal friction is desired), but such tendons may introduce an unacceptable amount of stretch for control processes relying on a direct relationship between actuator and joint position. Solid steel pull wires can also be used in or as transmission systems.

In accordance with an aspect of the current invention, control processes for the medical instruments of FIGS. 2, 3A, and 3B or instruments that otherwise have compliant transmission systems can employ remote measurements of the position of a mechanical joint to determine a tension to be applied to drive the mechanical joint. The control processes could also be employed for instruments having rigid transmission systems. FIG. 4 schematically shows a generalization of a medical instrument 400 having a mechanical joint 410 having a degree of freedom of motion corresponding to an angle or position θ. The term position is used broadly herein to include the Cartesian position, angular position, or other indication of the configuration of a degree of freedom of a mechanical system. A sensor (not shown) measures position θ at the remote joint 410 and provides measured position θ to a control system 450, for example, through a signal wire (not shown) extending from the sensor at the distal end of instrument 400, through the main tube (not shown) of instrument 400 to control system 450 at the proximal end of the instrument. The sensor may additionally measure a velocity $\dot{\theta}$ for the movement of joint 410, or velocity $\dot{\theta}$ may be determined from two or more measurements of position θ and the time between the measurements.

Joint 410 is connected through a transmission system 420 to an actuator 440, so that joint 410 is remote from actuator 440, e.g., joint 410 may be at a distal end of the instrument while actuator 440 is at the proximal end of the instrument. In the illustrated embodiment, transmission system 420 connects joint 410 so that a tension T applied by actuator 440 to transmission system 420 tends to rotate joint 410 in a clockwise direction. In general, transmission system 420 includes the entire mechanism used to transfer force from actuator 440 to joint 410, and actuator 440 may apply a force or torque to transmission system 420 which results in a tension in a cable or other component of transmission system 420. However, such a tension is generally proportional to the applied force or torque, so the term tension is intended to be used here without loss of generality to also indicate force or torque. It should also be noted that transmission system 420 may be (but is not required to be) so compliant that a direct relationship between the position of joint 410 and the position of actuator 440 would not be accurate enough for control of joint 410. For example, transmission system 420 may stretch, so that between a minimum and a maximum of tension T applied to transmission system 420, the difference in the effective length of transmission system 420 may correspond to 45° of joint articulation. In contrast, a typical medical device allows for stretching that corresponds to no more than a few degrees of joint articulation in order to be able to accurately model the position of the joint based on actuator position. It should be understood that in the general case compliance is not limited to a simple Hooke's law stretching of a spring structure. Transmission system 420 may include, for example, tendon 222 and at least a portion of backend mechanism 230 in the embodiment of FIG. 2 or tendon 322 and at least a portion of backend mechanism 330 in the embodiment of FIG. 3A. In general, the response of transmission system 420 to a tension T applied at a proximal end of transmission system 420 and to external forces applied to joint 410 or along the length of transmission system 420 may be difficult to model.

Actuator 440, which can include drive motor 242 or 342 of FIG. 2 or 3A, applies tension T to the proximal end of transmission system 420 and through transmission system 420 applies force or torque to joint 410, but other forces and torques are also applied to joint 410. In particular, one or more other transmission systems 420 may be connected to joint 410 and collectively apply a net tension or force that tends to cause joint 410 to rotate. In the illustrated embodiment of FIG. 4, a transmission system 422 is connected to joint 410 and to a drive motor 442, so that tension in transmission system 422 tends to oppose applied tension T and rotate joint 410 counterclockwise in FIG. 4. The additional transmission system 422 or transmission systems connected to joint 410 may be the same as transmission system 420, other than a difference in where the transmission systems 422 connect to joint 410.

Control system 450 can be a general purpose computer executing a program or a circuit wired to generate a drive signal that controls a tension T that actuator 440 applies to transmission system 420. When actuator 440 is an electrical motor, the drive signal may be a drive voltage or current that controls the torque output from actuator 440, and tension T is equal to the motor torque divided by the effective moment arm at which tension T is applied to transmission system 420. As described further below, control system 450 can calculate the magnitude of tension T or the motor torque using a desired position $\theta_D$, a desired velocity $\dot{\theta}_D$ for joint 410, and one or more measurements of position $\theta$ for joint 410 at the current and prior times. A user (e.g., a surgeon controlling system 400) can provide desired position $\theta_D$ and velocity $\dot{\theta}_D$ by manipulating a controller 460. The exact configuration of controller 460 is not critical to the present invention except that controller 460 is able to provide signals from which values for the desired position $\theta_D$ and velocity $\dot{\theta}_D$ can be determined. Manual controllers suitable for complex medical instruments generally provide signals that indicate many simultaneous instructions for movements of the medical instrument, and such movements may involve multiple joints in the instrument. Suitable manipulators for use as controller 460 are provided, for example, in the master controller of the da Vinci Surgical System available from Intuitive Surgical, Inc.

The tension T needed to move joint 410 from its current measured position $\theta$ to desired position $\theta_D$ in a time interval $\Delta t$ will generally depend on many factors including: the effective inertia of joint 410 that resists applied tension T; the inertia of actuator 440 which applies tension T, any other transmission systems 422 coupled to joint 410 and applying a net effective force; external forces applied to joint 410; internal and external frictional forces that oppose actuation of joint 410 or movement of transmission system; the current velocity $\dot{\theta}$ of joint 410; and internal and external damping forces. Many of these factors may vary depending on the working environment of instrument 400 and may be difficult to measure or model. However, models can be developed based on system mechanics or empirically for a particular joint in a medical instrument. In one specific embodiment, control system 450 determines the tension T from the distal joint errors $(\theta_D - \theta)$ and $(\dot{\theta}_D - \dot{\theta})$, which are respectively the difference between the measured and desired positions of joint 410 and the difference between measured and desired velocities of joint 410.

FIG. 5A is a flow diagram of a process 500 for controlling a medical instrument having the basic structure of system 400 of FIG. 4. Process 500 begins in step 510 by reading a current value of position $\theta$ of joint 410 and determining a current value for the joint velocity $\dot{\theta}$. Velocity $\dot{\theta}$ can be directly measured or determined or approximated in a well known manner using the current position $\theta$, a prior position $\theta'$, a time interval $\Delta t$ between measurements, for example, under the assumption of constant velocity (e.g., $\dot{\theta} = (\theta - \theta')/\Delta t$) or under the assumption of constant acceleration given a prior determination of velocity. Step 515 then acquires a desired position $\theta_D$ and a desired velocity $\dot{\theta}_D$ for joint 410, and step 520 computes a difference or error $(\theta_D - \theta)$ between the measured and desired positions and a difference or error $(\dot{\theta}_D - \dot{\theta})$ between the measured and desired velocities.

The position and velocity error computed in step 520 can be used to determine tension T required for joint 410 to reach the desired position $\theta_D$. In the embodiment of FIG. 5A, applied tension T may include multiple contributions, and the primary contribution is a distal tension $T_{DIST}$, which is determined as a function $f_1$ of position error $(\theta_D - \theta)$ and velocity error $(\dot{\theta}_D - \dot{\theta})$. Distal tension $T_{DIST}$ is independent of the position of the actuator, e.g., of the angle of the motor shaft, which allows determination of distal tension $T_{DIST}$ even when there is no direct relationship between the position of joint 410 and the position of actuator 440. In one particular embodiment, the function $f_1$ is of the form Equation 1, where g1 and g2 are gain factors, C is a constant or geometry dependent parameter, and $T_{sign}$ is a sign, i.e., ±1. Sign $T_{sign}$ is associated with movement of joint 410 produced by tension in transmission system 420 and may, for example, be positive (e.g., +1) if tension T in transmission system 420 tends to increase the position coordinate $\theta$ and negative (e.g., -1) if tension T in transmission system 420 tends to decrease the position coordinate $\theta$. In another embodiment, function $f_1$ imposes a lower bound on the force, for instance, in order for the force to be always positive and sufficient to avoid slack in the transmission system. The parameter C can be a constant selected according to known or modeled forces applied to joint 410 by other portions of the system. For example, parameter C may be a constant selected to balance the torque caused by other transmission systems applying force to joint 410 or may account for expected friction or external forces. However, parameter C is not required to strictly be a constant but could include non-constant terms that compensate for properties such as gravity or mechanism stiffness that can be effectively modeled, and accordingly, parameter C may depend on the measured joint position or velocity. The gain factors g1 and g2 can be selected according to the desired stiffness and dampening of joint 410. In particular, when joint 410 is used as a static grip, the net gripping force or torque applied to tissue depends on the term $g1(\theta_D-\theta)$ of Equation 1. In general, gain factors g1 and g2 and constant C can be selected according to the desired stiffness and dampening or responsiveness of joint 410 or according to an accumulation of error. For example, when inserting the instrument 400 to follow a natural lumen within a patient, the gain factor g1 can be set to a low value to make joint 410 behave gently and prevent joint 410 from harming surrounding tissue. After the insertion, the gain factor g1 can be set to a higher value that allows the surgeon to perform precise surgical task with the instrument.

$$F_1 = T_{sign} * (g1(\theta_D-\theta) + g2(\dot{\theta}_D-\dot{\theta}) + C) \qquad \text{Equation 1:}$$

The term $g1(\theta_D-\theta)+g2(\dot{\theta}_D-\dot{\theta})+C$ of Equation 1 can be used to approximately determine the torque, tension, or force currently required at joint 410 to rotate joint 410 to reach the desired position $\theta_D$ using transmission system 420 in a given time $\Delta t$. The torque and force or tension are related in that the torque is the product of the force and an effective movement arm R, which is defined by the perpendicular distance between the connection of transmission system 420 to joint 410 and the rotation axis of joint 410. The effective movement arm R can either be absorbed into gain factors g1 and g2 and constant C or used to convert a calculated distal tension $T_{DIST}$ into a calculated torque.

Distal tension $T_{DIST}$, with the proper choice of function $f_1$, e.g., proper selection of parameters g1, g2, and C in Equation 1, can approximate the force that actuator 440 is required to apply to move joint 410 in a manner that is responsive to manipulations by a human operator of manual controller 460. However, optional corrections are provided by steps 530, 535, 540, and 545 under some conditions. In particular, optional steps 530 and 535 respectively compute a saturated sum or integral I of the position error $(\theta_D-\theta)$ and calculate an integral tension $T_{INT}$. The integral tension $T_{INT}$, which may be positive, zero, or negative, can be added as a correction to distal tension $T_{DIST}$, which was calculated in step 525. Integral tension $T_{INT}$ is calculated as a function $f_2$ of saturated integral I and may simply be the product of integral I and a gain factor. The saturated integral I calculated in step 530 can simply be the sum for the past N intervals of position errors $(\theta_D-\theta)$ or differences $(\theta_{D,i}-\theta_{i-1})$ between the measured position at the end of the interval and the desired position that was to be achieved. The number N of intervals involved in the sum may be limited or not, and integral I may be saturated in that the magnitude of the integral is not permitted to exceed a maximum saturation value. The saturation value would generally be selected to cap the maximum or minimum value of integral tension $T_{INT}$. However, the minimum and maximum values of integral tension $T_{INT}$ can alternatively be capped when calculating the value of function $f_2$.

Figure 5B:
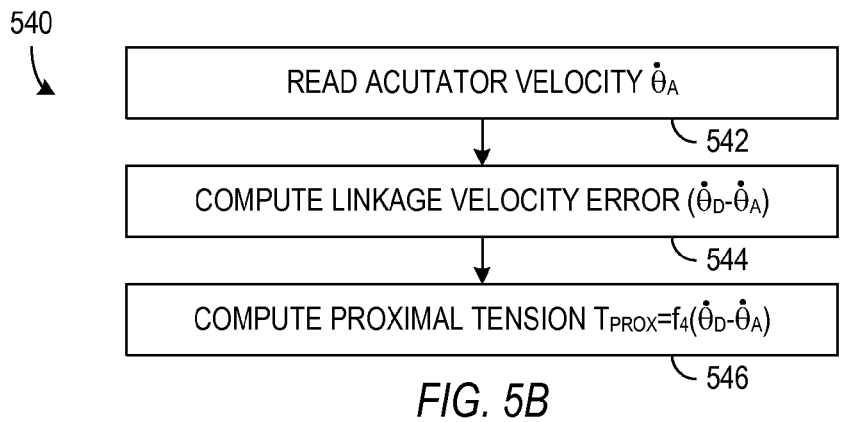
FIG. 5B is a flow diagram of a process for determining a tension correction associated with a difference between an actuator velocity and a joint velocity.

Optional step 540 computes another correction referred to herein as proximal tension $T_{PROX}$, which may be positive, zero, or negative. Proximal tension $T_{PROX}$ can be added to distal tension $T_{DIST}$, which was calculated in step 525. FIG. 5B is a flow diagram of a process 540 for computing proximal tension $T_{PROX}$. Process 540 begins in step 542 by reading a current value of a velocity $\dot{\theta}_A$ of actuator 440. Velocity $\dot{\theta}_A$ can be measured by a standard tachometer that attaches at the base of actuator 440. To improve computational efficiency, step 542 can also be scheduled to run between steps 510 and 515 of FIG. 5A. Step 544 then computes the proximal velocity difference or error $\dot{e}_{PROX}$, which is defined as the difference or error between a desired velocity computed based on desired velocity $\dot{\theta}_D$ of joint 410 and the current velocity computed based on the current actuator velocity $\dot{\theta}_A$. In one particular embodiment, the desired velocity can be the product of the effective moment arm R, sign $T_{sign}$, and desired velocity $\dot{\theta}_D$ of joint 410, while the current velocity can be the product of an effective moment arm of the actuator 440 and actuator velocity $\dot{\theta}_A$. In the embodiment of FIG. 5B, proximal tension $T_{PROX}$ is determined as a function $f_4$ of proximal velocity error $\dot{e}_{PROX}$. In one particular embodiment, the function $f_4$ may simply be the product of proximal velocity error $\dot{e}_{PROX}$ and a gain factor. The gain factor can be selected to provide an additional dampening effect to transmission system 420.

Figure 5C:
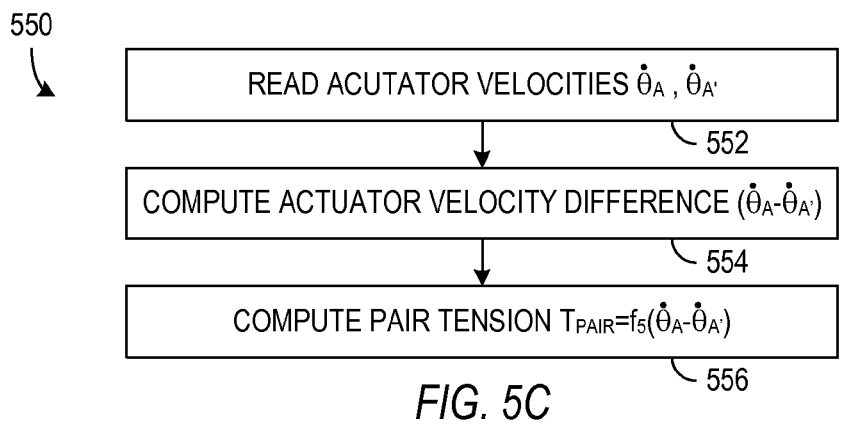
FIG. 5C is a flow diagram of a process for determining a tension correction associated with a difference between the velocities of actuators manipulating the same joint.
Figure 6:
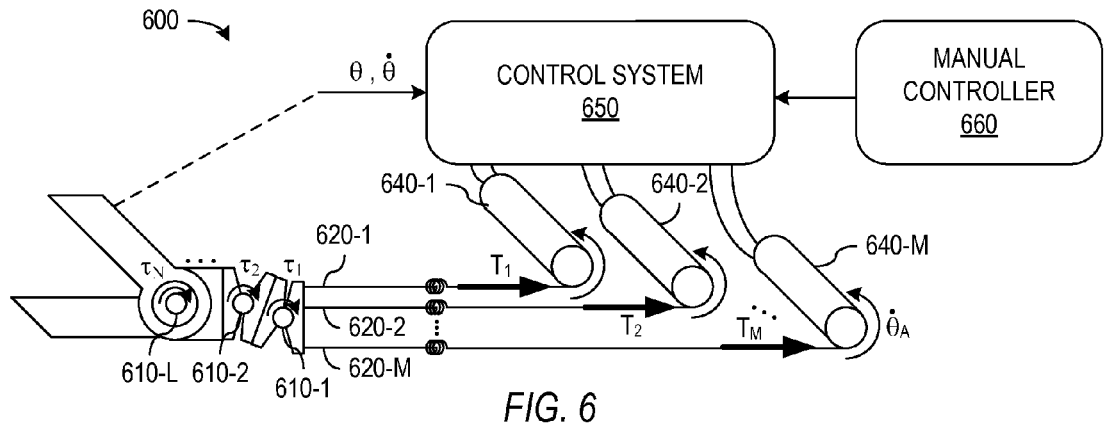
FIG. 6 schematically illustrates a robotic medical system and particularly shows quantities used in an embodiment of the invention that controls a multi jointed instrument.

Optional step 550 of FIG. 5A computes a pair tension $T_{PAIR}$, which may be positive, zero, or negative correction to distal tension $T_{DIST}$, which was calculated in step 525. FIG. 5C is a flow diagram of a process 550 for computing the pair tension $T_{PAIR}$. Process 550 begins in step 552 by reading a current value of velocity $\dot{\theta}_A$ of actuator 440 and velocity values of all other actuators associated with joint 410. In the system of FIG. 4, there are two actuators 440 and 442 coupled to joint 410 and two actuator velocities $\dot{\theta}_A$ and $\dot{\theta}_{A'}$. Step 552 can be scheduled to run between steps 510 and 515 of FIG. 5A to improve computational efficiency. Step 556 then computes a pair velocity difference or error $\dot{e}_{PAIR}$, which can be defined as the difference or error between the current velocities $\dot{\theta}_A$ and $\dot{\theta}_{A'}$ of the actuators 440 and 442 associated to joint 410, when actuators 440 and 442 are substantially identical, e.g., have the same effective moment arms for operation on respective transmission systems 420 and 422. In one particular embodiment, the current velocity error $\dot{e}_{PAIR}$ can be the product of the difference $(\dot{\theta}_A-\dot{\theta}_{A'})$ and the effective moment arm of actuators 440 and 442. In the embodiment of FIG. 6, pair tension $T_{PAIR}$ is determined as a function $f_5$ of pair velocity error $\dot{e}_{PAIR}$. In one particular embodiment, the function $f_5$ may simply be the product of pair velocity error $\dot{e}_{PAIR}$ and a gain factor. The gain factor can be selected to provide additional dampening effect to transmission system 420.

Tension T is determined in step 560 of FIG. 5A as a function $f_3$ of sum of distal tension $T_{DIST}$, proximal tension $T_{PROX}$, pair tension $T_{PAIR}$, and integral tension $T_{INT}$. In the embodiment of FIG. 5C, function $f_3$ limits the maximum and minimum values of tension T. Maximum tension $T_{MAX}$ and minimum tension $T_{MIN}$ can be set in the programming of control system 450 (e.g., in software). However, a compliant transmission system may itself have a minimum or maximum tension with proper design in the backend mechanism. For example, a transmission system illustrated in FIG. 3A has a minimum tension $T_{MIN}$ controlled by the setting of preload system 333 or 335 when motor/actuator 342 or 344 is freewheeling and a maximum tension $T_{MAX}$ resulting from slipping when the torque of the couple motor 342 or 344 exceeds the point when the tendon 322 or 324 slips on capstan 332 or 334. In general, it is desirable to have maximum and minimum tensions $T_{MAX}$ and $T_{MIN}$ set by both hardware and software. In particular, maximum tension $T_{MAX}$ should be set to avoid damage to the instrument resulting from large forces, and tension $T_{MIN}$ should be set to ensure that tendons in the transmission system do not slack and become derailed or tangled.

Step 565 of FIG. 5A generates a control signal that causes actuator 440 to apply tension T calculated in step 560. For example, the control signal when actuator 440 is a direct drive electrical motor may be a drive current that is controlled to be proportional to calculated tension T. Control system 450 in step 570 causes actuator 440 to apply and hold the calculated tension T for a time interval Δt, during which time, joint 410 moves toward the current desired position $\theta_D$. When changing the tension T, the application of the full tension T will be delayed by a time depending on the inertia of actuator 440. Preferably, the inertia of actuator 440 is relatively small for rapid response. For example, the inertia of a drive motor acting as actuator 440 would preferably be less than five times the inertia of joint 410. After time Δt, process 500 branches back to step 510 to repeat measurement of the joint position, acquisition of the target position and velocity, and calculation of the tension T to be applied during the next time interval. In general, time Δt should be small enough to provide motion that appears to be smooth to the operator of the instrument and which does not cause undesirable vibrations in the instrument. For example, calculating and setting tension T two hundred and fifty times per second or more will provide movement that appears smooth to the human eye and will provide instrument operation that is responsive to human commands, e.g., to human manipulation of controller 460. Use of the errors in the calculation of the tension T will generally cause joint 410 to converge on the desired positions with or without the computation of integral tension $T_{INT}$ and without detailed modeling or measurement of the instrument or the external environment. However, as described above, parameters such as gains g1 and g2 used in calculating the applied tension T can be tuned for specific instruments and further tuned in use to compensate for changes in the external environment of the instrument.

Figure 5D:
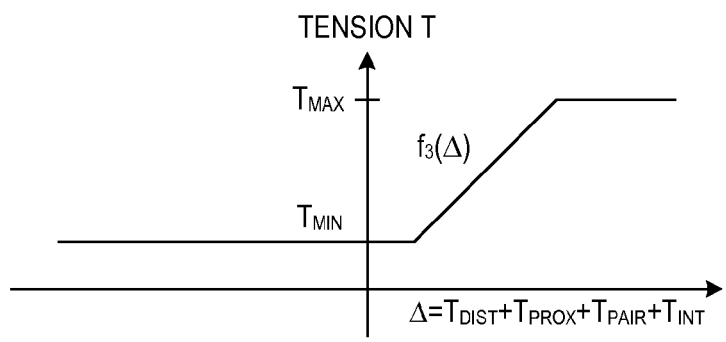
FIG. 5D illustrates a function for control of a maximum and minimum applied tension.

The tension that actuator 442 applies to transmission system 422 can also be controlled using control process 500 of FIG. 5A, and parameters use in process 500 for actuator 442 and transmission system 422 can be the same or different from those used for actuator 440 and transmission system 420 based on the similarities and differences of actuator 442 and transmission system 422 when compared to actuator 440 and transmission system 420. In particular, the sign value $T_{sign}$ for actuator 442 in the configuration of FIG. 4 will be opposite to the sign value $T_{sign}$ for actuator 440 because transmission systems 422 and 420 connect to rotate joint 410 in opposite directions. As a result, the primary tension contribution $T_{DIST}$ calculated in step 525 will typically be negative for one actuator 440 or 442. Step 560, which calculates the applied tension T, can set a negative tension sum $T_{DIST}+T_{PROX}+T_{PAIR}+T_{INT}$ to the minimum tension $T_{MIN}$ as shown in FIG. 5D. Accordingly, parameters, e.g., constant C, for the calculation of distal tension $T_{DIST}$ in step 525 can generally be selected based on the assumption that the other actuator will apply the minimum tension $T_{MIN}$.

The principles described above for control of a single joint in a medical instrument can also be employed to simultaneously control multiple joints in an instrument. FIG. 6 schematically illustrates a multi jointed medical instrument 600 and some quantities used in control processes for instrument 600. Instrument 600 includes L joints 610-1 to 610-L, generically referred to herein as joints 610. Each joint 610 provides a range of relative positions or orientations of adjacent mechanical members and typically has one or two degrees of freedom of motion as described further below. Joints 610 of instrument 600 provide a total of N degrees of freedom, where the number N of degrees of freedom is greater than or equal to the number L of joints 610, and the configurations of degrees of freedom of joints 610 can be described using N-components or a vector θ. An N-component velocity vector $\dot{\theta}$ is associated with the vector θ. Torques $\tau_1$ to $\tau_N$, which move joints 610-1 to 610-L, respectively correspond to the N components of vector θ in that torques $\tau_1$ to $\tau_N$ tend to cause respective components of vector θ to change.

Joints 610 are actuated using M transmission systems 620-1 to 620-M (generically referred to herein as transmission systems 620) and M actuators 640-1 to 640-M (generically referred to herein as actuators 640). Transmission systems 620 and actuators 640 can be similar or identical to transmission systems 420 and actuators 440, which are described above with reference to FIG. 4. In general, the number M of transmission systems 620 and actuators 640 is greater than the number N of degrees of freedom, but the relationship between M and N depends on the specific medical instrument and the mechanics of joints in the instrument. For example, a joint 610 providing a single degree of freedom of motion may be actuated using two transmission systems 620, and a joint 610 providing two degrees of freedom may be actuated using three or four transmission systems 620. Other relationships between degrees of freedom and actuating transmission systems are possible. Control system 650 operates actuators 640-1 to 640-M to select respective tensions $T_1$ to $T_M$ that actuators 640-1 to 640-M respectively apply to transmission systems 620-1 to 620-M.

Control system 650 for instrument 600 can use a distal sensor (not shown) to determine position and velocity vectors θ and $\dot{\theta}$ associated with joints 610. (Position and velocity are used here to include the values and movement of linear or angular coordinates.) Control system 650 also determines desired position and velocity vectors $\theta_D$ and $\dot{\theta}_D$ of joints 610. As described further below, the desired position and velocity vectors $\theta_D$ and $\dot{\theta}_D$ depend on input from a manual controller 660 that may be manipulated by a surgeon using instrument 600. In general, the desired position and velocity vectors $\theta_D$ and $\dot{\theta}_D$ will further depend on the criteria or constraints defined in the control process implemented using control system 650.

FIG. 7 illustrates a control process 700 in accordance with an embodiment of the invention for controlling a multi jointed instrument such as instrument 600 of FIG. 6. Process 700 begins in step 710 by reading the joint position vector θ from one or more position sensors in the instrument. The velocity vector $\dot{\theta}$ can be determined using a direct measurement of joint movement or through calculation of the change in position measurements between two times. Control system 650 receives a surgeon's instructions in step 715. The surgeon's instructions can indicate a desired position and velocity of a specific working portion of the instrument. For example, a surgeon through manipulation of manual control 660 can indicate a desired position, velocity, orientation, and rotation of the distal tip or end effector of the instrument such as described in U.S. Pat. No. 6,493,608, entitled "Aspects of a Control System of a Minimally Invasive Surgical Apparatus," which is incorporated herein by reference. Step 720 then converts the instructions from manual controller 660 into desired position and velocity vectors $\theta_D$ and $\dot{\theta}_D$ for joints 610. For example, given the desired position, orientation, velocity, and angular velocity of the distal tip of instrument 600 of FIG. 6, control system 650 can calculate desired joint position and velocity vectors $\dot{\theta}_D$ and $\dot{\theta}_D$ that will achieve the desired tip configuration. The conversion step 720 can be achieved with well-known techniques, such as differential kinematics inversion as described by "Modeling and Control of Robot Manipulators," L. Sciavicco and B. Siciliano, Springer, 2000, pp. 104-106 and "Springer Handbook of Robotics," Bruno Siciliano & Oussama Khatib, Editors, Springer, 2008, pp. 27-29, which are incorporated herein by reference. Above-referenced U.S. Pat. No. 6,493,608, entitled "Aspects of a Control System of a Minimally Invasive Surgical Apparatus," also describes techniques for determining desired joint position and velocity vectors $\dot{\theta}_D$ and $\dot{\theta}_D$ that will achieve the desired tip configuration. It should be noted that for instruments with a kinematic redundancy, i.e., if the number of degrees of freedom of motion provided by joints 610 is larger than the number of degrees of freedom of the motion command specified by manual controller 660, the redundancy can be resolved with standard techniques such as those described in Yoshihiko Nakamura, "Advanced Robotics: Redundancy and Optimization," Addison-Wesley (1991).

It should also be appreciated that software enforced constraints between the joints of the instruments can also be enforced when solving the inverse kinematics problem on the desired command for the instrument. For instance, the joint positions and velocity commands of two joints can be forced to be the same or opposite or in a given ratio, effectively implementing a virtual cam mechanism between the joints.

Step 725 computes a position error vector $(\theta_D-\theta)$ and velocity error vector $(\dot{\theta}_D-\dot{\theta})$, and step 730 uses components of error vectors $(\theta_D-\theta)$ and $(\dot{\theta}_D-\dot{\theta})$ for calculation of respective torque components $\tau_1$ to $\tau_N$. In one specific embodiment, each torque component $\tau_i$ for an index i from 1 to N is determined using Equation 2. In Equation 2, $g1_i$ and $g2_i$ are gain factors, and $C_i$ is a constant or geometry-dependent parameter that may be selected according to known or modeled forces applied to the joint by other portions of the system. However, parameter $C_i$ is not required to strictly be a constant but could include non-constant terms that compensate for properties such as gravity or mechanism stiffness that can be effectively modeled, and accordingly, $C_i$ may depend on the measured position or velocity of the joint 610-$i$ on which the torque $\tau_i$ acts. In general, gain factors $g1_i$ and $g2_i$ and constant $C_i$ can be selected according to the desired stiffness and dampening or responsiveness of a joint or according to an accumulation of error. For example, when inserting the instrument 600 to follow a natural lumen within a patient, the gain factor $g1_i$ can be set to a low value to make a joint behave gently and prevent the joint action from harming surrounding tissue. After the insertion, the gain factor $g1_i$ can be set to a higher value that allows the surgeon to perform a precise surgical task with the instrument. Other equations or corrections to Equation 2 could be employed in the determination of the torque. For example, the calculated torque could include a correction proportional to a saturated integral of the difference between the current measurement of joint position and the desired joint position that the previously applied torque was intended to achieve. Such correction using a saturated integral could be determined as described above for the single joint control process of FIG. 5A and particularly illustrated by steps 530 and 535 of FIG. 5A.

$$\tau_i = g1_i(\theta_D-\theta)_i + g2_i(\dot{\theta}_D-\dot{\theta})_i + C_i \quad \text{Equation 2:}$$

Step 735 uses the torques computed in step 730 to determine distal tensions $T_{DIST}$. Distal tension $T_{DIST}$ is an M component vector corresponding to transmission systems 620-1 to 620-M and actuators 640-1 to 640-M. The determination of the distal tensions depends on geometry or mechanics between the instrument joints and transmission systems. In particular, with multiple joints, each joint may be affected not only by the forces applied directly by transmission systems attached to the joint but also by transmission systems that connect to joints closer to the distal end of the instrument. The torques and tensions in a medical instrument can generally be modeled using equations of the form of Equation 3. In Equation 3, $\tau_1$ to $\tau_N$ are components of the torque vector, and $T_1$ to $T_M$ are the distal tensions respectively in M transmission systems 620 that articulate joints 610. Each coefficient $a_{IJ}$ for index I=1 to N and index J=1 to M generally corresponds to the effective moment arm of the tension $T_J$ for joint and rotation axis corresponding to torque $\tau_I$.

$$\begin{bmatrix} \tau_1 \\ \tau_2 \\ \vdots \\ \tau_N \end{bmatrix} = \begin{bmatrix} a_{11} & a_{12} & \cdots & a_{1M} \\ a_{21} & a_{22} & \cdots & a_{2M} \\ \vdots & \vdots & \ddots & \vdots \\ a_{N1} & a_{N2} & \cdots & a_{NM} \end{bmatrix} \begin{bmatrix} T_1 \\ T_2 \\ \vdots \\ T_N \end{bmatrix} = A \begin{bmatrix} T_1 \\ T_2 \\ \vdots \\ T_N \end{bmatrix} \quad \text{Equation 3}$$

The computation in step 735 thus corresponds to solving N equations for M variables $T_1$ to $T_M$. Since M is generally greater than N, the solution is not unique, so that inequality constraints can be selected, such as the constraint that all tensions are greater than a set of minimum values, and optimality conditions, such as the condition that a set of tensions of lowest maximum value is chosen, can be applied to provide a unique solution with desired characteristics such as minimal tensions that stay above a desired threshold in all or selected joints. The matrix inversion problem of Equation 3 with inequality and optimality constraints such as minimal tension constraints can be solved by some well-known techniques such as the SIMPLEX method of linear programming. (See, for example, "Linear Programming 1: Introduction," George B. Dantzig and Mukund N. Thapa, Springer-Verlag, 1997, which is incorporated herein by reference in its entirety.) In accordance with a further aspect of the invention, the distal tensions can be determined using a process that sequentially evaluates joints beginning with the most distal joint and solves for tensions in transmission systems that connect to each joint based on geometric parameters and the tensions previously calculated for more distal joints.

Control system 650 in one embodiment of process 700 activates actuators 640 to apply the distal tensions calculated in step 735 to respective transmission systems 620. Alternatively, corrections to the distal tensions can be determined as illustrated by steps 740 and 745. In particular, step 740 computes a correction tension $T_{PROX}$, which depends on the difference between a desired transmission velocity vector $\dot{\theta}_{DL}$, computed based on desired joint velocity $\dot{\theta}_D$, and a current transmission velocity vector $\dot{\theta}_L$, computed based on the current actuator velocity $\dot{\theta}_A$. In one particular embodiment, the desired transmission velocity can be the multiplication of the transpose of the coupling matrix A in Equation 3 with the desired joint velocity $\dot{\theta}_D$, while the current transmission velocity can be the product of the actuator velocity BA and respective moment arm of actuators 640. Correction tension $T_{PROX}$ can compensate for inertia or other effects between the actuator 640 and the connected joint 610 and, in one embodiment, is a function of the difference $(\dot{\theta}_{DL}-\dot{\theta}_L)$ such as the product of difference $(\dot{\theta}_{DL}-\dot{\theta}_L)$ and a gain factor. Step 745 computes a correction tension $T_{PAIR}$, which depends upon a difference or differences between the velocities of actuators that actuate the same joint. For example, in the case in which a joint provides one degree of freedom of motion and is actuated by a pair of actuators connected to the joint through a pair of transmission systems, correction tension $T_{PAIR}$ can be determined as a function of the difference between the velocities of the two actuators. (See, for example, step 550 of FIG. 5A as described above.) Corrections similar to correction tension $T_{PAIR}$ can be generalized to the case where three or more transmission systems and actuators actuate a joint having two degrees of freedom of motion.

Step 750 combines distal tension $T_{DIST}$ and any corrections $T_{PROX}$ or $T_{PAIR}$ to determine a combined tension T applied by the actuators. In general, each component $T_1$ to $T_M$ of the combined tension T can be limited to saturate at a maximum tension $T_{MAX}$ or a minimum tension $T_{MIN}$ if the sum of the calculated distal tensions $T_{DIST}$ and corrections $T_{PROX}$ and $T_{PAIR}$ is greater than or less than the desired maximum or minimum values as described above with reference to FIG. 5D. Steps 755 and 760 then activate actuators 640 to apply and hold the combined tension T for a time interval $\Delta t$ before process 700 returns to step 710 and reads the new joint positions. Holding the tension for an interval of roughly 4 ms or less, which corresponds to a rate of 250 Hz or higher, can provide smooth movement of an instrument for a medical procedure.

Medical instruments commonly require that the working tip or end effector of the instrument have a position and orientation that an operator such as a surgeon can control. On the other hand, the specific position and orientation of each joint is generally not critical to the procedure being performed, except where joint position or orientation is mandated by the lumen through which the instrument extends. In accordance with an aspect of the invention, one approach to control a multi joint instrument selects tensions applied through tendons using differences between current and desired configurations of the tip of an instrument. For example, differences between the measured position, orientation, velocity, and angular velocity of the tip of the instrument and the desired position, orientation, velocity, and angular velocity of the tip of the instrument can control the tensions applied to tendons of a medical instrument.

Figure 7A:
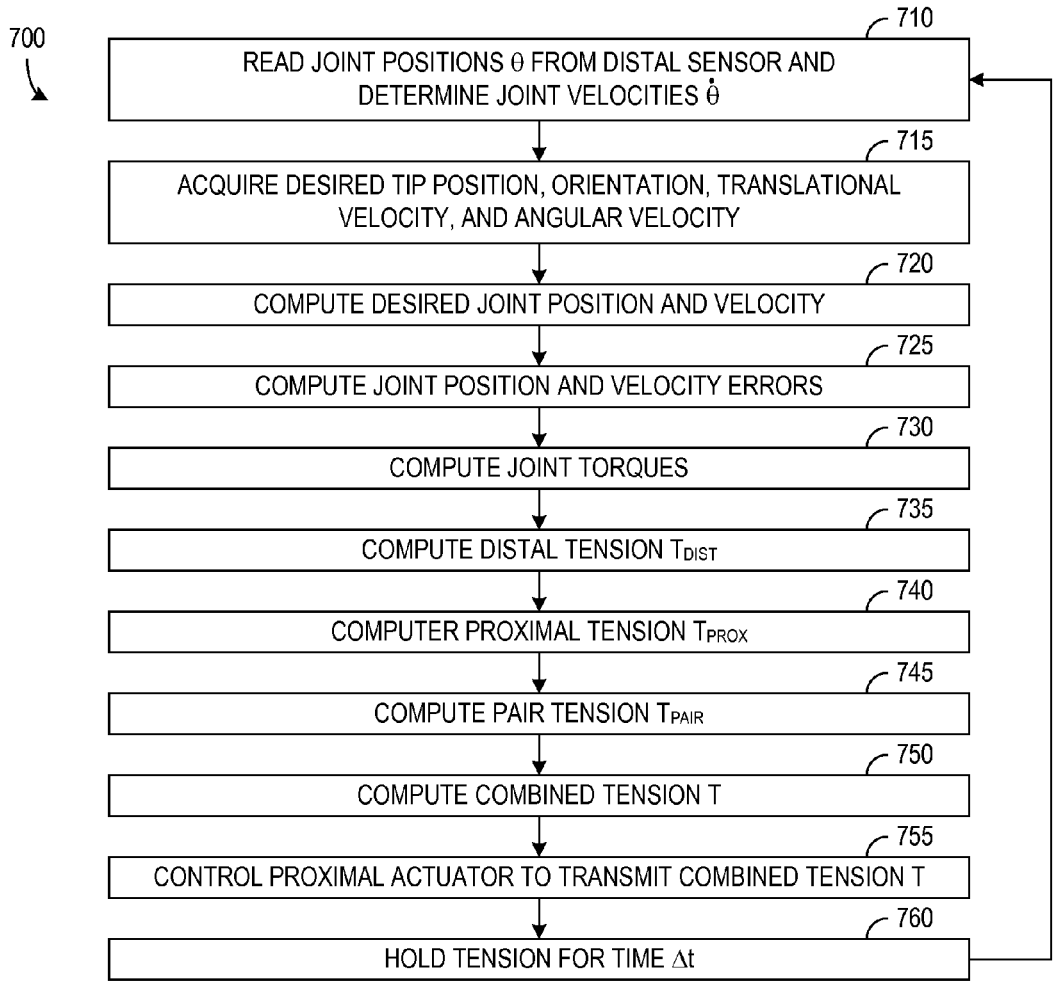
FIG. 7A is a flow diagram of a process in accordance with an embodiment of the invention that selects applied tensions based on differences between measured and desired joint configurations.
Figure 7B:
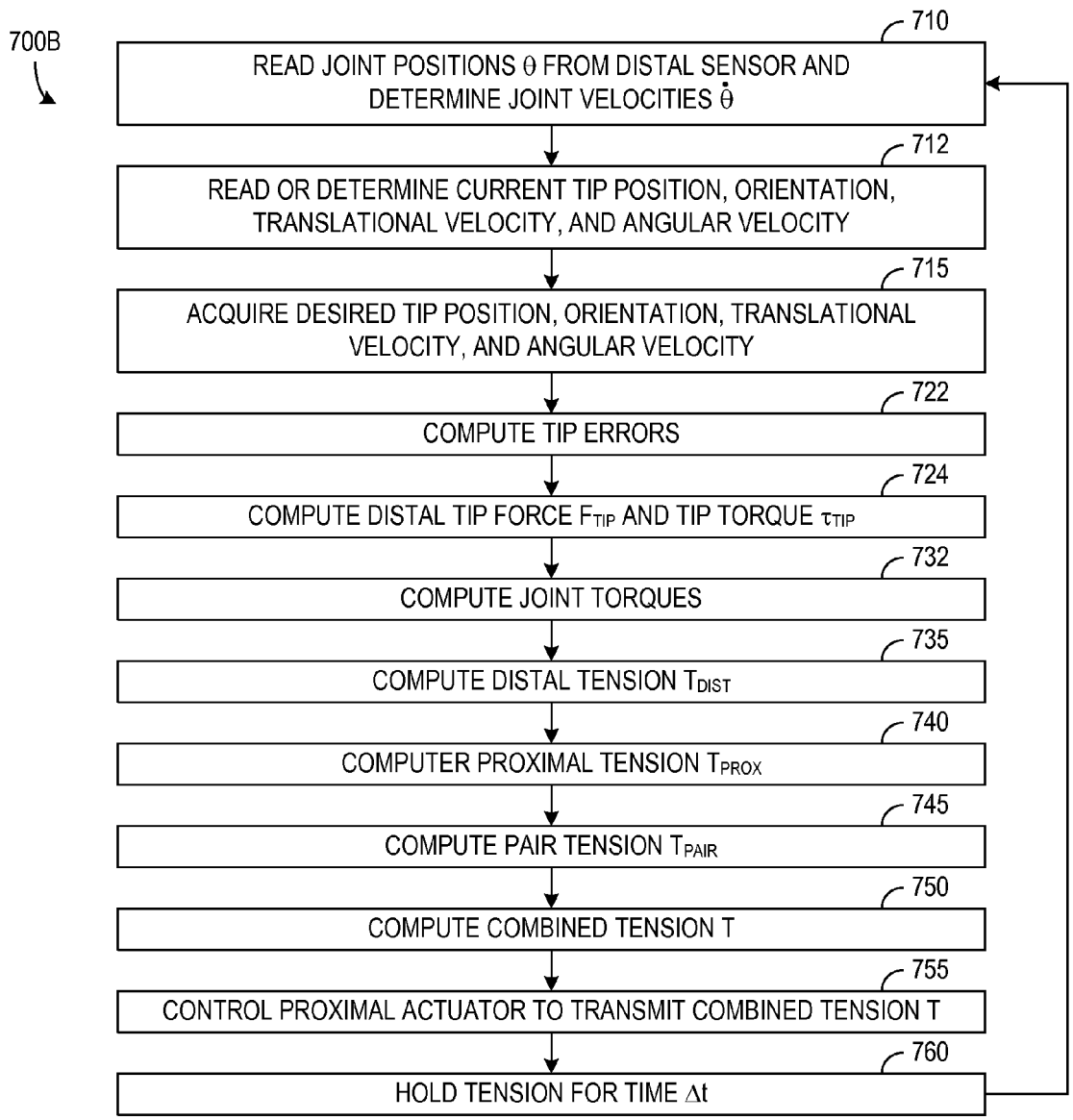
FIG. 7B is a flow diagram of a process in accordance with an embodiment of the invention that selects applied tensions based on differences between measured and desired tip configurations.

FIG. 7B illustrates a control process 700B in accordance with an embodiment of the invention. Process 700B employs some of the same steps as process 700, and those steps have the same reference numbers in FIGS. 7A and 7B. Process 700B in step 710 reads or determines the joint positions $\theta$ and joint velocities $\dot{\theta}$ from a sensor or sensors in the medical instrument and in step 712 reads or determines a position, orientation, velocity, and angular velocity of a tip of the instrument. Tip here refers to a specific mechanical structure in the instrument and may be an end effector such as forceps, scissors, a scalpel, or a cauterizing device on the distal end of the instrument. In general, the tip has six degrees of freedom of motion and has a configuration that can be defined by six component values, e.g., three Cartesian coordinates of a specific point on the tip and three angles indicating the pitch, roll, and yaw of the tip. Velocities associated with changes in the configuration coordinates over time may be directly measured or calculated using measurements at different times. Given joint positions and velocities $\theta$ and $\dot{\theta}$ and a priori knowledge of the kinematic model of the instrument 610, one can build both forward and differential kinematic models that allow computing the Cartesian position, orientation, translational velocity, and angular velocity of the tip with respect to the frame of reference of the instrument 610. The forward and differential kinematic model of a kinematic chain can be easily constructed according to known methods. For instance, the procedure described by John J. Craig, "Introduction to Robotics: Mechanics and Control," Pearson Education Ltd. (2004), which is incorporated herein by reference, may be used. Step 715 determines the desired tip position, orientation, translational velocity, and angular velocity, which can be performed in the manner described above.

In another embodiment, a sensor, for example, a shape sensor, may be used to directly measure Cartesian position and orientation as described in U.S. Pat. App. Pub. No. 20090324161 entitled "Fiber optic shape sensor" by Giuseppe M. Prisco, which is incorporated herein by reference. Translational velocities associated with changes in the configuration coordinates over time may be calculated using measurements at different times. Unlike the translational velocities, the angular velocities cannot be computed simply by the differencing approach due to the angular nature of the quantities. However, the methods of computing the angular velocities associated with the changes in orientation are known in the art and described, for example, by L. Sciavicco and B. Siciliano, "Modelling and Control of Robot Manipulators," Springer 2000, pp. 109-111.

Process 700B in step 722 calculates tip errors. In one embodiment, step 722 includes calculating a position error or difference $e_{POS}$ between the desired Cartesian coordinates of the tip and the current Cartesian coordinates of the tip, a translational velocity error or difference $e_{VT}$ between the desired translational velocity of the tip and the current translational velocity of the tip, an orientation error or difference $e_{ORI}$ between the desired orientation coordinates of the tip and the current orientation coordinates of the tip, and an angular velocity error or difference $e_{VA}$ between the desired angular velocity of the tip and the current angular velocity of the tip. Unlike the position error $e_{POS}$, the orientation error $e_{ORI}$ cannot be computed simply by the differencing approach due to the angular nature of the quantities. However, the methods of computing the change in orientation are known in the art and can be found in robotics literatures, for example, L. Sciavicco and B. Siciliano, "Modelling and Control of Robot Manipulators," Springer, 2000, pp. 109-111.

In step 724, process 700B determines a tip force $F_{TIP}$ and a tip torque $\tau_{TIP}$ that are intended to move tip from the current configuration to the desired configuration. In this embodiment of the invention, tip force $F_{TIP}$ depends on errors $e_{POS}$ and $e_{VT}$. For example, each component $F_X$, $F_Y$, or $F_Z$ of tip force $F_{TIP}$ can be calculated using Equation 4, where $gp_i$ and $gv_i$ are gain factors and $Cf_i$ is a constant. The tip torque $T_{TIP}$ can be determined in a similar manner, in which each component of tip torque $\tau_i$ is a function of errors $e_{ORI}$ and $e_{VA}$ with another set of gain factors and constants $gori_i$, $gva_i$, and $C\tau_i$ as shown in Equation 5. In general, the gain factors $gp_i$ and $gv_i$ associated with different force or torque components $F_i$ and $\tau_i$ can be different. Having separate gain factors and constants for each component of tip force $F_{TIP}$ and tip torque $\tau_i$ provides flexibility in specifying the dynamic behavior of the end effector or instrument tip, enhancing more effective instrument interaction with the tissue. For instance, when navigating the instrument into a small lumen, one may set low values for the gain factors of tip force perpendicular to the inserting direction while have high values for the gain factors along the inserting direction. With that, the instrument is sufficient stiff for insertion while having low lateral resistance to the tissue, preventing damage to the surrounding tissue. Another example, when using the instrument to punch a hole in the tissue in certain direction, having high values in the gain factors of the tip torque as well as the gain factor along the inserting direction of the tip force, facilitate the hole-punch task.

$$F_i = gp_i * e_{POS} + gv_i * e_{VT} + Cf_i \quad \text{Equation 4:}$$

$$\tau_i = gori_i * e_{ORI} + gva_i * e_{VA} + C\tau_i \quad \text{Equation 5:}$$

Step 732 determines a set of joint torques that will provide the tip force $F_{TIP}$ and tip torque $\tau_{TIP}$ determined in step 724. The relationships between joint torque vector $\tau$, tip force $F_{TIP}$, and tip torque $\tau_{TIP}$ are well-documented and normally described as in Equation 6, where $J^T$ is the transpose of the well-known Jacobian Matrix J of a kinematic chain of the instrument.

$$\tau = J^T \begin{bmatrix} F_{TIP} \\ \tau_{TIP} \end{bmatrix} \quad \text{Equation 6}$$

The Jacobian Matrix J depends on the geometry of the instrument and the current joint positions determined in step 710 and can be constructed using known methods. For example, John J. Craig, "Introduction to Robotics: Mechanics and Control," Pearson Education Ltd. (2004), which is incorporated herein by reference, describes techniques that may be used to construct the Jacobian Matrix for a robotic mechanism. In some cases, if there are extra or redundant degrees of freedom of motion provided in the medical instrument, e.g., more than the six degrees of freedom of motion of the tip, the set of joint torques that provides tip force $F_{TIP}$ and tip torque $T_{TIP}$ is not unique, and constraints can be used to select a set of joint torques having desired properties, e.g., to select a set of joint torques that prevents the joints reaching their mechanical joint limits in range of motion or supported loads or to enforce extra utility on any particular joints of the instrument during manipulation. For instance, one can prevent the joints reaching their mechanical joint limits by selecting a set of joint torques that minimizes the deviation from the midrange joint positions, from the null space associated with the transpose of Jacobian matrix $J^T$. The set of joint torques can be selected according to Equation 7. In Equation 7, $P(\theta)$ is a potential function that define addition utility to be provided by the solution, $\nabla$ is a gradient operator, $N(\ )$ is a null space projection operator that selects a set of joint torques from the null space of the transpose of Jacobian matrix $J^T$, associated with its input. In one embodiment, potential $P(\theta)$ a quadratic function of the joint positions that has a minimum when the joints are in the center of their range of motion. The gradient of the potential function $-\nabla P(\theta)$ selects a set of joint torques that draws joints moving toward the center of their range of motion while the null space projection operator $N(\ )$ enforces that the selected set of joint torques providing the desired tip force and tip torques also satisfy the additional utility. Techniques for using constraints in robotic systems providing redundant degrees of freedom of motion are known in the art and can be found in robotics literatures. See, for instance, Yoshihiko Nakamura, "Advanced Robotics: Redundancy and Optimization," Addison-Wesley (1991) and literature by Oussama Khatib, "The Operational Space Framework," JSME International Journal, Vol. 36, No. 3, 1993.

$$\tau = J^T \begin{bmatrix} F_{TIP} \\ \tau_{TIP} \end{bmatrix} + N(-\nabla P(\theta)) \quad \text{Equation 7}$$

Process 700B after step 732 proceeds in the same manner as process 700 described above. In particular, based on the joint torques determined in step 732, step 735 determines tensions $T_{DIST}$. Steps 740 and 745 determine corrections $T_{PROX}$ and $T_{PAIR}$ to tensions $T_{DIST}$, and step 750 determines a combined tension vector T. Steps 755 and 760 then apply and hold the components of combined tension vector T on the transmission systems to actuate the medical instrument during a time interval $\Delta t$.

Processes 700 and 700B of FIGS. 7A and 7B required determination of tensions that will produce a particular set of joint torques. The tendon tension for a single isolated joint can be determined from a joint torque simply by dividing the joint torque by the moment arm at which the tension is applied. In the multi joint case, due to geometry of the transmission system and cable routing and redundancy in the actuation cable, the problem amounts to solving a system of equations with constraints. In one particular embodiment, one may apply non-negative tendon tension constraints (or minimum tension constraints) when solving the system of equations to prevent slacking in the cables or other tendons in the transmission systems. The inputs of the problem are the determined joint torque for each joint while the geometry of cable routing defines the system of equations (or the coupling matrix A of Equation 3). Appropriate tendon tensions are needed that fulfill Equation 3 and are larger than minimum tension constraints. A standard optimization method, called SIMPLEX method can be used to handle this matrix inverse problem with inequality and optimality constraints. The SIMPLEX method requires a relatively larger computation time and may not be advantageous to be used in real time application. Also, the SIMPLEX method does not guarantee continuity in the solutions as the joint torques change. To speed-up the computation efficiency and provide a continuous output solution, an iterative approach can be considered which relies on the triangular nature of the coupling matrix A. FIGS. 8A, 8B, 8C, 9A, 9B, 9C, 9D, and 9E illustrate a few specific examples of joints in multi jointed instruments and are used herein to illustrate some properties of the coupling matrix A in Equation 3.

Figure 8A:
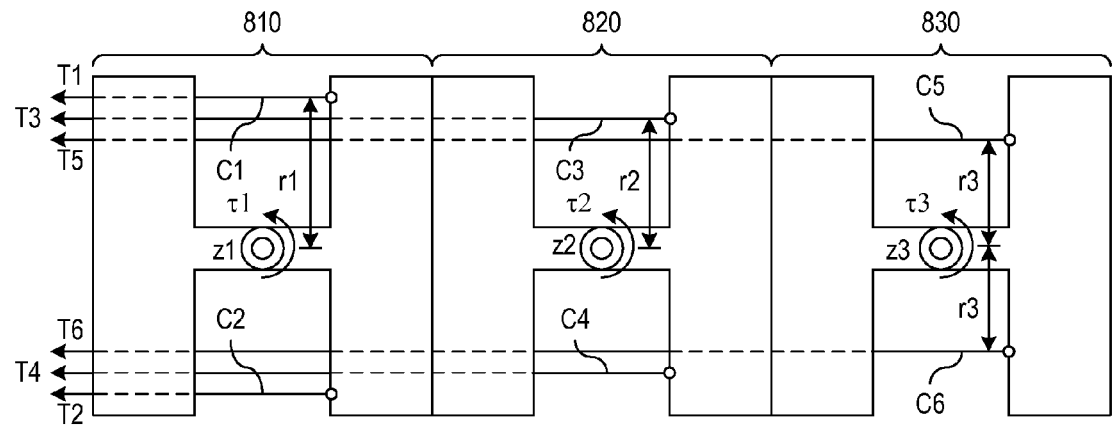
FIG. 8A is a side view of a portion of a multi jointed instrument that can be operated using drive force control in accordance of an embodiment of the invention to control joints with parallel actuation axes.

FIG. 8A, for example, illustrates a portion of an instrument that includes multiple mechanical joints 810, 820, and 830. Each joint 810, 820, or 830 provides a single degree of freedom, which corresponds to rotation about an axis z1, z2, or z3 of the joint. In FIG. 8A, tendons C1 and C2 connect to joint 810 for actuation of joint 810. Tendons C3 and C4 pass through joint 810 and connect to joint 820 for actuation of joint 820. Tendons C5 and C6 pass through joints 810 and 820 and connect to join 830 for actuation of joint 830. The proximal ends (not shown) of tendons C1 to C6 can be connected though compliant transmission systems such as illustrated in FIG. 2 or 3A to respective drive motors or other actuators. The control system for the instrument controls the actuators to apply respective tensions T1, T2, T3, T4, T5, and T6 in tendons C1, C2, C3, C4, C5, and C6.

Joint 830 is at the distal end of the instrument in the illustrated embodiment, and actuation of joint 830 could be controlled using a single-joint process such as described above with reference to FIGS. 5A, 5B, 5C, and 5D. However, the total torque on joint 820 depends not only on the tensions in cables C3 and C4 but also the torque applied by tendons C5 and C6, which are connected to joint 830. The total torque on joint 810 similarly depends not only on the tensions in tendons C1 and C2 but also the torque applied by tendons C3, C4, C5, and C6, which are connected to joints 820 and 830 that are closer to the distal end. Models based on the geometric or kinematic characteristics of the instrument can be developed to relate the torques T1, T2, and T3 on joints 810, 820, and 830 to the tension in tendons T1, T2, T3, T4, T5, and T6. Equation 3A illustrates one such mathematical model and provides a specific example of Equation 3 above. In Equation 3A, $\tau_1$, $\tau_2$, and $\tau_3$ are the respective actuating torques on joints 810, 820, and 830, $r_1$, $r_2$, and $r_3$ are the effective moment arms at which tendons C1, C3, and C5 attach, and T1, T2, T3, T4, T5, and T6 are the tensions in respective tendons C1, C2, C3, C4, C5, and C6. The model that leads to Equation 3A applies to a specific set of geometric or mechanical characteristics of the instrument including joints 810, 820, and 830 including that: rotation axes z1, z2, and z3 are parallel and lie in the same plane; tendons C1 and C2, C3 and C4, or C5 and C6 respectively attach at effective moment arm r1, r2, or r3; and tendons C1, C3, and C5 operate on respective joints 810, 820, and 830 in rotation directions opposite from the operation of tendons C2, C4, and C6, respectively.

$$\begin{bmatrix} \tau_1 \\ \tau_2 \\ \tau_3 \end{bmatrix} = \begin{bmatrix} r_1 & -r_1 & r_2 & -r_2 & r_3 & -r_3 \\ 0 & 0 & r_2 & -r_2 & r_3 & -r_3 \\ 0 & 0 & 0 & 0 & r_3 & -r_3 \end{bmatrix} \cdot \begin{bmatrix} T1 \\ T2 \\ T3 \\ T4 \\ T5 \\ T6 \end{bmatrix} \quad \text{Equation 3A}$$

Figure 8B:
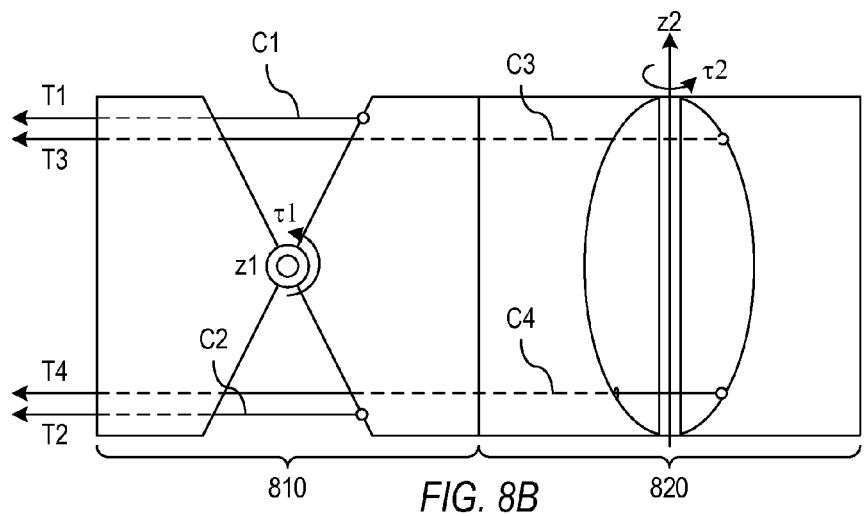
FIGS. 8B and 8C respectively show side and end views of a portion of a multi jointed instrument having joints with perpendicular actuation axes that can be operated using drive force control in accordance with an embodiment of the invention.
Figure 8C:
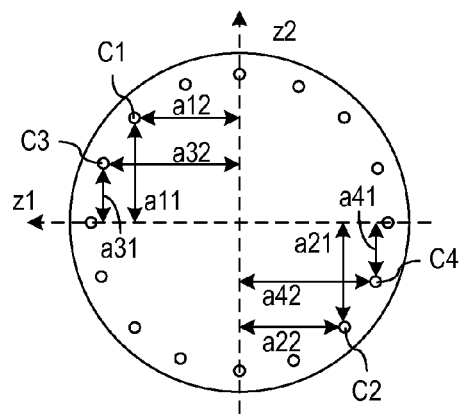

FIGS. 8B and 8C illustrate characteristics of a medical instrument including joints 810 and 820 with respective rotation axes z1 and z2 that are perpendicular to each other. In general, the net torque at each joint 810 and 820 depends on the tensions in the tendons passing through the joint to the distal end and the effective moment arms associated with the tendons relative to the actuation axis of the joint. FIG. 8C shows a view of a base of joint 810 to illustrate a typical example in which each tendon C1, C2, C3, and C4 operates at different moment arms about axes z1 and z2. Considering joints 810 and 820 as an isolated system or the last two actuated joints on the distal end of an instrument, the net torques $\tau_1$ and $\tau_2$ on joints 810 and 820 are related to the tensions T1, T2, T3, and T4 in respective tendons C1, C2, C3, and C4 as indicated in Equation 3B. In particular, joint 820 is subject to a net torque $\tau_2$ that depends on tension T3 in tendon C3 and a moment arm a32 relative to axis z2 at which tendon C3 attaches to joint 820 and the tension T4 in tendon C4 and a moment arm a42 relative to axis z2 at which tendon C4 attaches to joint 820. Torque $\tau_1$ on joint 810 depends on the tensions T1 and T2 in the tendons C1 and C2 attached to joint 810, the tensions T3 and T4 in the tendons C3 and C4 attached to joint 820, and the moment arms a11, a21, a31, and a41. Moment arms a21 and a41 are assigned with a negative sign because pulling tendons C2 and C4 creates the rotation in a direction opposite from the convention-defined positive direction for torque $\tau_1$ on joint 810. For the same reason, moment arm a31 is also assigned with a negative sign as pulling tendon C3 causes rotation opposite to the direction of positive rotation of joint 820.

$$\begin{bmatrix} \tau_1 \\ \tau_2 \end{bmatrix} = \begin{bmatrix} a11 & -a21 & a31 & -a41 \\ 0 & 0 & -a32 & a42 \end{bmatrix} \begin{bmatrix} T1 \\ T2 \\ T3 \\ T4 \end{bmatrix} \quad \text{Equation 3B}$$

It should be appreciated that a similar method to compute the matrix A in Equations 3 can be employed when the joint axes are neither parallel or perpendicular to each other but rather at an arbitrary relative orientation, by computing accordingly the moment arms of each tendon with respect to each joint axis.

Figure 9A:
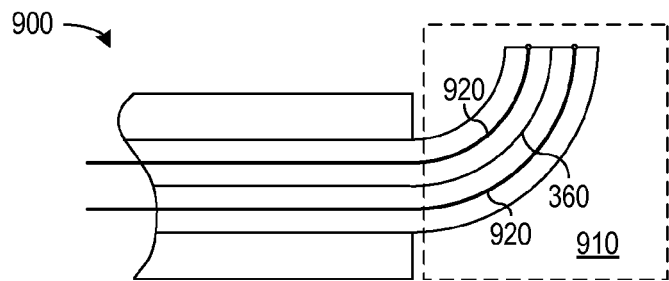
FIG. 9A shows an embodiment of the invention in which a joint includes a continuously flexible structure that provides two degrees of freedom of motion.
Figure 9B:
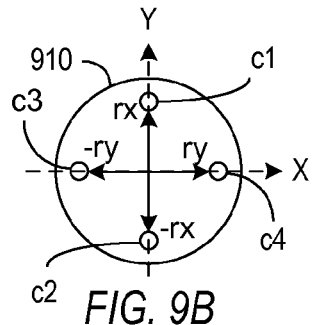
FIGS. 9B and 9C illustrate embodiments of the invention respectively employing four and three tendons to control two degrees of freedom of motion in the joint of FIG. 9A.

FIG. 9A shows a portion 900 of an instrument including a continuous flexible joint 910 such as is commonly found in medical catheters, endoscopes for the gastrointestinal tract, the colon and the bronchia, guide wires, and some other endoscopic instruments such as graspers and needles used for tissue sampling. Joint 910 is similar to the flexible structure described above with reference to FIG. 3B. However, joint 910 is manipulated through the use of three or more tendons 920 to provide a joint with two degrees of freedom of motion. For example, FIG. 9B shows a base view of an embodiment in which four tendons 920, which are labeled c1, c2, c3, and c4 in FIG. 9B, connect to an end of flexible joint 910. A difference in the tensions in tendons c1 and c2 can turn joint 910 in a first direction, e.g., cause rotation about an X axis, and a difference in the tensions in tendons c3 and c4 can turn joint 910 in a second direction that is orthogonal to the first direction, e.g., cause rotation about a Y axis. The components $\tau_X$ and $\tau_Y$ of the net torque tending to bend joint 910 can be determined from tensions T1, T2, T3, and T4 respectively in tendons c1, c2, c3, and c4 as indicated in Equation 3C. As can be seen from Equation 3C, equations for torque components $\tau_X$ and $\tau_Y$ are not coupled in that component $T_X$ depends only on tensions T1 and T2 and component $\tau_Y$ depends only on tensions T3 and T4.

$$\begin{bmatrix} \tau_X \\ \tau_Y \end{bmatrix} = \begin{bmatrix} rx & -rx & 0 & 0 \\ 0 & 0 & ry & -ry \end{bmatrix} \begin{bmatrix} T1 \\ T2 \\ T3 \\ T4 \end{bmatrix} \quad \text{Equation 3C}$$

Figure 9C:
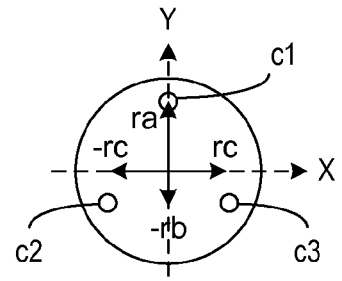

FIG. 9C illustrates a base view of an embodiment that uses three tendons 920, which are labeled c1, c2, and c3 in FIG. 9C, to actuate joint 910. With this configuration, the components $\tau_X$ and $\tau_Y$ of the net torque tending to bend joint 910 can be determined from tensions T1, T2, and T3 respectively in tendons c1, c2, and c3 as indicated in Equation 3D where ra is the moment arm of tendon c1 about the X axis, −rb is the moment arm of tendons c2 and c3 about the X axis, and rc and −rc are the respective moment arms of tendons c2 and c3 about the Y axis. Moment arms of tendons c2 and c3 about X-axis are assigned with a negative sign by convention because pulling tendons c2 and c3 will bend joint 910 in a direction opposite from the direction that pulling tendon c1 bends joint 910 about the X axis. For the same reason, the moment arm of tendon c3 about Y-axis is assigned a negative sign by convention.

$$\begin{bmatrix} \tau_X \\ \tau_Y \end{bmatrix} = \begin{bmatrix} ra & -rb & -rb \\ 0 & rc & -rc \end{bmatrix} \begin{bmatrix} T1 \\ T2 \\ T3 \end{bmatrix} \quad \text{Equation 3D}$$

Figure 9D:
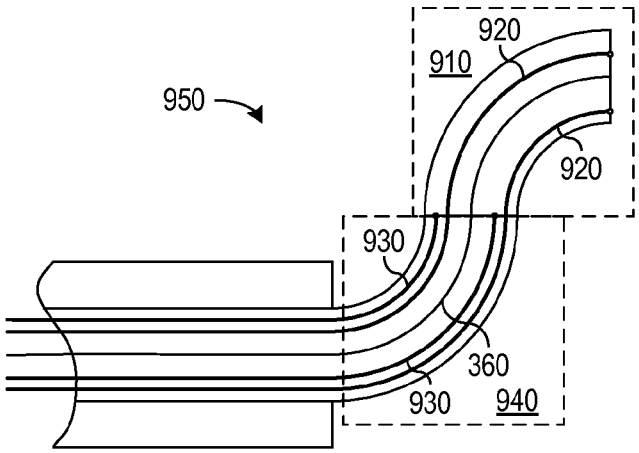
FIG. 9D shows an embodiment of a two jointed medical instrument in which each joint includes a continuously flexible structure and provides two degrees of freedom of motion.
Figure 9E:
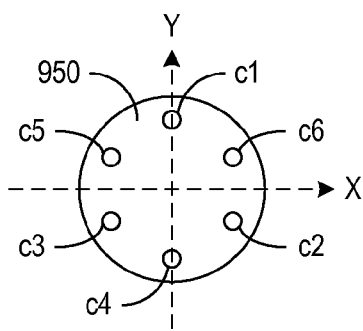
FIG. 9E illustrates an embodiment of the invention employing six tendons to control four degrees of freedom of motion provided by the two joints in the instrument of FIG. 9D.

FIG. 9D illustrates an embodiment in which a flexible instrument 950, e.g., a flexible catheter, contains two joints. A joint 910 is actuated through tendons 920 to provide two degrees of freedom of motion, and a joint 940 is actuated through tendons 930 to provide another two degrees of freedom of motion. FIG. 9E illustrates the base of joint 940 in a specific case that uses three tendons 920 (labeled c1, c2, and c3 in FIG. 9E) for joint 910 and three tendons 930 (labeled c4, c5, and c6 in FIG. 9E) for joint 940. The relationships between torques and forces in the most distal joint 910 may be modeled using Equation 3D above. However, the torques in joint 940 depend on the tensions in all of the tendons 920 and 930 that pass through flexible section 940. The torques and tensions in instrument 950 may thus be related in one specific example as indicated in Equation 3E. In Equation 3E, $\tau 1_x$ and $\tau 1_y$ are torque components in joint 910, $\tau 2_x$ and $\tau 2_y$ are torque components in joint 940, ra, rb, and rc are the magnitudes of moment arms, T1, T2, and T3 are tensions in tendons 920, and T4, T5, and T6 are tensions in tendons 930.

$$\begin{bmatrix} \tau 2_X \\ \tau 2_Y \\ \tau 1_X \\ \tau 1_X \end{bmatrix} = \begin{bmatrix} -ra & rb & rb & ra & -rb & -rb \\ 0 & -rc & rc & 0 & rc & -rc \\ 0 & 0 & 0 & ra & -rb & -rb \\ 0 & 0 & 0 & 0 & rc & -rc \end{bmatrix} \begin{bmatrix} T1 \\ T2 \\ T3 \\ T4 \\ T5 \\ T6 \end{bmatrix} \quad \text{Equation 3E}$$

Equations 3A to 3E illustrate that in many medical instruments the problem of finding tensions that provide a particular torque in the most distal joint can be solved independently of the other tensions in the system. More generally, the joint torque for each joint depends on the tensions in the tendons that connect to that joint and on the tensions applied to more distal joints. Step 735 of processes 700 and 700B of FIGS. 7A and 7B can thus be performed using a process that iteratively analyzes joints in a sequence from the distal end of the instrument toward the proximal end of the instrument to determine a set of tensions that produces a given set of joint torques.

Figure 10:
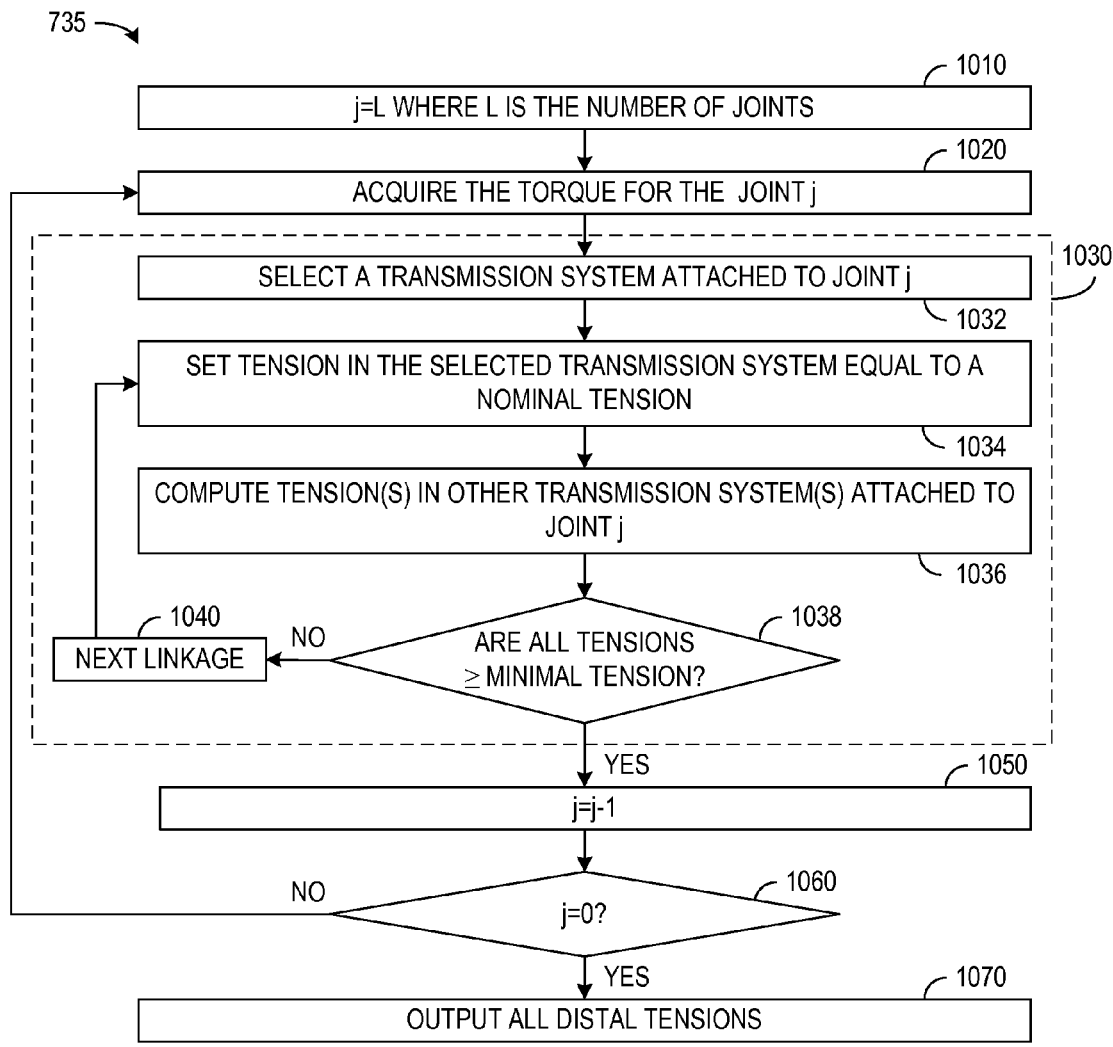
FIG. 10 is a flow diagram illustrating a process in accordance with an embodiment of the invention that determines tensions through sequential evaluation of joints in a multi jointed instrument.

FIG. 10 shows an iterative process 735 for computing tensions that produce a given set of joint torques. Process 735 in the embodiment of FIG. 10 starts with a tension determination for the last or most distal joint and then sequentially determines tensions for joints in an order toward the first or most proximal joint. Step 1010 initializes an index j, which identifies a joint for analysis and is initially set to the number L of joints. Step 1020 then acquires the torque $\tau_j$ for the jth joint. The joint torque $\tau_j$ may, for example, be determined as in step 730 of process 700 or step 732 of 700B as described above and may have a single non-zero component for a joint providing a single degree of freedom of motion or two non-zero components for a joint providing two degrees of freedom of motion.

Step 1030 then calculates the tensions to be directly applied to the jth joint through the linkages attached to the jth joint in order to produce the net torque, e.g., computed in step 730 or 732 of FIG. 7A or 7B. In the example of FIG. 10, computation of step 1030 is under the constraint that one of the directly applied tensions is a target or nominal tension. The nominal tension may be but is not required to be zero so that tension in the transmission system is released or alternatively the minimum tension that ensures that the tendons in the transmission systems do not become slack. The nominal tension may but is not required to correspond to a case in which actuator force is released, e.g., where drive motors 640 of FIG. 6 are freewheeling, in which case the tension may depend on type of transmission system employed.

In the specific case in which jth joint in the medical instrument provides a single degree of freedom of motion and is directly coupled to two tendons or transmission systems, the joint torque has a single component that is related to the tensions by a single equation from among Equations 3. Step 1030 for the Lth or most distal joint then involves solving a linear equation relating the joint torque to the two tensions coupled to the most distal joint. With a single linear equation involving two unknown tensions, applying the constraint that one tension is the nominal tension guarantees a unique solution for the other tension. In particular, the other tension can be uniquely determined from the torque on the most distal joint and the relevant coefficients of the coupling matrix A. Alternatively, if the Lth joint provides two degrees of freedom of motion and is coupled to three tendons or transmission systems, the joint torque has two components and corresponds to two equations from among Equations 3. The two equations involve three tensions, so that with the constraint that one of the tensions be equal to the nominal tension, the other two tensions can be uniquely determined from the components of the joint torque and the relevant components of the coupling matrix A. It should be noted that the proposed method is general in the sense that, in a similar fashion, if m tendons, with m greater than three, are connected to the same joint that provides two degrees of freedom, then (m−2) tensions can be constrained at the same time to be equal to the nominal tension, while the remaining two tensions will be uniquely determined from the components of the joint torque and the relevant components of the coupling matrix A.

Step 1030 is initially executed for the most distal joint (i.e., j=L). Substep 1032 of step 1030 initially selects one of the transmission systems attached to the most distal joint, and substep 1034 sets that tension to the nominal tension for a trial calculation in substep 1036. Substep 1036 initially calculates tension (or tensions) for the other transmission systems attached to the joint, and the calculated tensions only depend on the computed joint torque and the other tensions directly applied to the most distal joint. Step 1038 determines whether all of the calculated tensions are greater than or equal to the minimum permitted tension. If not, step 1040 selects another of the transmission systems directly coupled to the joint to be the transmission system with the nominal tension when steps 1034 and 1036 are repeated. Once step 1040 determines that the calculated tension or tensions are all greater than or equal to the minimum allowed tension, the determination of the tension for the most distal joint is complete, and step 1050 decrements the joint index j before process 735 branches back from step 1060 for repetition of step 1020.

Step 1030 for the jth joint in the case of a joint connected to two transmission systems and providing one degree of freedom of motion involves evaluation of a single equation from among Equations 3. As described above, the nature of the coupling matrix A is such that the equation for the jth joint involves only the tensions directly coupled to the Jth joint and the tensions coupled to more distal joints. Accordingly, if the tensions for more distal joints have already been determined, the equation associated with the jth joint involves only two unknowns, which are the tensions in the transmission systems directly connected to the joint. The constraint that one of the tensions be the nominal tension allows unique determination of the other tension that is larger than or equal to the nominal tension. The case where the jth joint connects to three transmission systems and provides two degrees of freedom of motion involves evaluation of the two equations associated with the two components of the joint torque. If the tensions for more distal joints have already been determined, the equations associated with the jth joint involves only three unknowns, which are the tensions in the tendons directly connected to the joint. The constraint that one of the tensions be the nominal tension allows unique determination of the other two tensions that are larger than or equal to the nominal tension.

Process 735 of FIG. 10 can thus use tension determinations in the order of the joints from the distal end of the instrument to generate a complete set of distal tensions that is output in step 1070 when step 1060 determines that the most proximal joint has been evaluated. Process 735 can be efficiently implemented using a computer or other computing system operating for real time determination of tensions that are changed at a rate that provides motion smooth enough for medical procedures, e.g., at rates of up to 250 Hz or more. Further, the constraint that each joint have at least one directly applied tension at a target or nominal value provides continuity between the tensions determined at successive times.

The processes described above can be implemented or controlled using software that may be stored on computer readable media such as electronic memory or magnetic or optical disks for execution by a general purpose computer. Alternatively, control of or calculations employed in the above-described processes can be implanted using application-specific hardware or electronics.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A medical instrument system comprising a medical instrument, the system including:
   a plurality of joints;
   a plurality of actuators;
   a plurality of transmission systems having proximal ends respectively coupled to the actuators, each transmission system of the plurality of transmission systems having a distal end attached to an associated one of the plurality of joints to allow transmission of a force for articulation of the medical instrument system;
   a sensor coupled to measure a configuration of the medical instrument; and
   a control system coupled to
      receive configuration data, including a current configuration of a tip of the medical instrument from the sensor, and including a desired configuration of the tip of the medical instrument,
      determine a difference between the desired configuration and the current configuration of the tip of the medical instrument,
      determine, from the difference, a tip force and a tip torque that when applied to the tip of the medical instrument move the tip of the medical instrument from the current configuration toward the desired configuration,
      determine joint torques for one or more of the plurality of joints that produce the determined tip force and the determined tip torque;
      determine a set of tensions based on the determined joint torques, but not based on positions of the plurality of actuators; and
      generate control signals for at least one of the plurality of actuators that cause the at least one of the plurality of actuators to apply the determined set of tensions to at least one of the plurality of transmission systems.

2. The system of claim 1 wherein the control system is further coupled to hold the set of tensions for a predetermined time interval.

3. The system of claim 1,
   wherein determining the difference includes determining a first difference between a current value of a first position coordinate of the tip and a desired value of the first position coordinate of the tip; and
   wherein determining the tip force includes determining a first product of the first difference and a first gain factor and using the first product in determining a first component of the tip force.

4. The system of claim 3,
   wherein determining the difference further includes determining a second difference between a current value of a second position coordinate of the tip and a desired value of the second position coordinate of the tip; and
   wherein determining the tip force further includes determining a second product of the second difference and a second gain factor, wherein the second gain factor is different from the first gain factor, and using the second product in determining a second component of the tip force.

5. The system of claim 1,
   wherein determining the difference includes determining a first difference between a current value of a first angular coordinate of the tip and a desired value of the first angular coordinates of the tip; and
   wherein determining the tip force includes determining a first product of the first difference and a first gain factor, and using the first product in determining a first component of the tip torque.

6. The system of claim 5,
   wherein determining the difference further includes determining a second difference between a current value of a second angular coordinate of the tip and a desired value of the second angular coordinate of the tip; and
   wherein determining the tip force further includes determining a second product of the second difference and a second gain factor, wherein the second gain factor is set to be different from the first gain factor, and using the second product in determining a second component of the tip force.

7. The system of claim 1, wherein determining the tip force comprises:
   determining a difference between a component of a current velocity of the tip and a component of a desired velocity of the tip;
   determining a product of the difference and a gain factor; and
   using the product in determining a component of the tip force.

8. The system of claim 1, wherein determining the tip force comprises:
   determining a difference between an angular velocity of the tip and a desired angular velocity of the tip;
   determining a product of the difference and a gain factor; and
   using the product in determining a component of the tip force.

9. The system of claim 1, wherein the plurality of joints provide more than six degrees of freedom of motion, including degrees of freedom of motion that are redundant for movement of the tip; and wherein the joint torques are computed to keep the joints away from limits of ranges of motion of the joints or away from joint torque limits.

10. The system of claim 1 wherein the sensor is an optical fiber shape sensor.

11. The system of claim 1, wherein the control system regulates the set of tensions applied to the transmission systems to be independent of a compliance of the transmission systems or the joints.

12. The system of claim 1, wherein the control system regulates the set of tensions applied to the transmission systems to be independent of a length of the transmission systems from their proximal ends to their distal ends.

13. The system of claim 1, wherein the control system regulates the set of tensions applied to the transmission systems to be independent of shape of the transmission systems from their proximal ends to their distal ends.

14. A method for controlling a medical instrument, the method comprising:
   measuring a configuration for a plurality of joints of the medical instrument;
   receiving a command indicating a desired configuration of the medical instrument;
   determining tensions respectively in a plurality of transmission systems that respectively connect a plurality of actuators to the plurality of joints, wherein determining tensions is independent of positions of the actuators and includes
      determining a difference between a desired configuration and a current configuration of a tip of the medical instrument,
      determining from the difference, a tip force and a tip torque that when applied to the tip of the medical instrument moves the tip of the medical instrument from the current configuration toward the desired configuration,
      determining joint torques for one or more of the plurality of joints that produce the determined tip force and the determined tip torque, and
      determining a set of tensions based on the determined joint torques, but not on positions of the plurality of actuators; and
   generating control signals for at least one of the plurality of actuators that cause the at least one of the plurality of actuators to apply the determined set of tensions to at least one of the plurality of transmission systems.

15. The method of claim 14,
   wherein determining the difference includes determining a first difference between a current value of a first position coordinate of the tip and a desired value of the first position coordinate of the tip; and
   wherein determining the tip force includes determining a first product of the first difference and a first gain factor and using the first product in determining a first component of the tip force.

16. The method of claim 15,
   wherein determining the difference further includes determining a second difference between a current value of a second position coordinate of the tip and a desired value of the second position coordinate of the tip; and
   wherein determining the tip force further includes determining a second product of the second difference and a second gain factor, wherein the second gain factor is different from the first gain factor, and using the second product in determining a second component of the tip force.

17. The method of claim 14,
   wherein determining the difference includes determining a first difference between a current value of a first angular coordinate of the tip and a desired value of the first angular coordinates of the tip; and
   wherein determining the tip force includes determining a first product of the first difference and a first gain factor and using the first product in determining a first component of the tip torque.

18. The method of claim 17,
   wherein determining the difference further includes determining a second difference between a current value of a second angular coordinate of the tip and a desired value of the second angular coordinate of the tip; and
   wherein determining the tip force further includes determining a second product of the second difference and a second gain factor, wherein the second gain factor is set to be different from the first gain factor, and using the second product in determining a second component of the tip force.

19. The method of claim 14, wherein determining the tip force comprises:
   determining a difference between a component of a current velocity of the tip and a component of a desired velocity of the tip;
   determining a product of the difference and a gain factor; and
   using the product in determining a component of the tip force.

20. The method of claim 14, wherein determining the tip force comprises:
   determining a difference between an angular velocity of the tip and a desired angular velocity of the tip;
   determining a product of the difference and a gain factor; and
   using the product in determining a component of the tip force.

* * * * *